United States Patent [19]

Bachmair et al.

[11] Patent Number: 5,646,017

[45] Date of Patent: *Jul. 8, 1997

[54] METHODS OF GENERATING DESIRED AMINO-TERMINAL RESIDUES IN PROTEINS

[75] Inventors: Andreas Bachmair, Cologne, Germany; Daniel Finley, Cambridge; Alexander Varshavsky, Boston, both of Mass.

[73] Assignee: Massachusetts Institute of Technology, Cambridge, Mass.

[*] Notice: The term of this patent shall not extend beyond the expiration date of Pat. No. 5,093,242.

[21] Appl. No.: 473,180

[22] Filed: Jun. 7, 1995

Related U.S. Application Data

[63] Continuation of Ser. No. 239,800, May 9, 1994, Pat. No. 5,496,721, which is a continuation of Ser. No. 988,807, Dec. 10, 1992, abandoned, which is a continuation of Ser. No. 821,720, Jan. 15, 1992, Pat. No. 5,196,321, which is a continuation of Ser. No. 356,378, May 24, 1989, Pat. No. 5,093,242, which is a continuation-in-part of Ser. No. 178,924, Apr. 7, 1988, Pat. No. 5,132,213, which is a continuation-in-part of Ser. No. 103,910, Oct. 1, 1987, abandoned, which is a continuation-in-part of Ser. No. 915,151, Oct. 2, 1986, abandoned.

[51] Int. Cl.⁶ .......................... C12N 15/62; C12N 15/63; C07K 14/435; C12P 21/04
[52] U.S. Cl. ............... 435/69.7; 435/252.3; 435/252.33; 435/254.11; 530/350
[58] Field of Search ........................ 435/240.2, 240.1, 435/252.33, 240.4, 254.11, 252.3, 69.1, 69.7; 530/350; 935/33, 34, 38, 47

[56] References Cited

U.S. PATENT DOCUMENTS

| 5,093,242 | 3/1992 | Bachmair et al. | 435/69.7 |
| 5,108,919 | 4/1992 | Liu et al. | 435/224 |
| 5,132,213 | 7/1992 | Bachmair et al. | 435/69.7 |
| 5,156,968 | 10/1992 | Liu | 435/224 |
| 5,196,321 | 3/1993 | Bachmair et al. | 435/69.7 |
| 5,496,721 | 3/1996 | Bachmair et al. | 435/240.2 |

FOREIGN PATENT DOCUMENTS

| WO88/02406 | 4/1988 | WIPO . |
| WO89/12678 | 12/1989 | WIPO . |

OTHER PUBLICATIONS

Nagai and Thorgersen, *Nature* 309: 810 (1984).
Hershko et al., *Proc. Natl. Acad. Sci. USA* 81: 7021 (1985).
Tsunasawa et al., *J. Biol. Chem.* 260: 5382 (1985).
Boissel et al., *Proc. Natl. Acad. Sci. USA* 82: 8448 (1985).
Thornton et al., *J. Mol Biol.* 167: 443 (1983).
Ferber et al., *J. Biol. Chem.* 261: 3128 (1986).
Bachmair et al., *Science* 234: 179 (1986).
Ferber et al., *Nature* 326: 808 (1988).
Reiss et al., *J. Biol. Chem.* 263: 2693 (1988).
Townsend et al., *J. Exp. Med.* 168: 1211 (1988).
Miller et al., *Biotechnology* 1: 698 (1989).
Chau et al., *Science* 243: 1576 (1989).
Gonda et al., *J. Biol. Chem.* 264: 16700 (1989).
Bachmair and Varshavsky, *Cell* 56: 1019 (1989).
Ozkaynak et al. EMBO J. 6(5) 1429–1439 1987.

*Primary Examiner*—Mindy Fleisher
*Assistant Examiner*—Nancy J. Degen
*Attorney, Agent, or Firm*—Kevin M. Farrell

[57] ABSTRACT

Methods of designing or modifying protein structure at the protein or genetic level to produce specified amino-termini in vivo or in vitro are described. The methods can be used to alter the metabolic stability and other properties of the protein or, alternatively, to artificially generate authentic amino-termini in proteins produced through artificial means. The methods are based upon the introduction of the use of artificial ubiquitin-protein fusions, and the discovery that the in vivo half-life of a protein is a function of the amino-terminal amino acid of the protein.

1 Claim, 10 Drawing Sheets

FIGURE 3a

```
                        Ser
                        Ala
                        Thr
                        Val
                        Gly
   ubiquitin      ▼     Cys      Gln      β-galactosidase
  ⌒⌒⌒⌒⌒⌒       Cys
  Met⌒⌒⌒Gly ── Met  ─   His ∿∿∿∿∿∿∿∿∿∿∿∿∿∿∿ Lys
                        Ile
                        Glu
                        Tyr
                        Gln
                        His
                        Phe
                        Leu
                        Trp
                        Asp
                        Asn
                        Lys
                        Arg
                       [Pro]
```

FIGURE 3b

▼
MQIFV ···· RLRGG ─ MHGSGAWLLPVSLVKRKTTLAPN ····· VWCQK ubiquitin                      β-galactosidase (76 aa)                        (1045 aa)

a b c d

| Construct. type | Half-life |
|---|---|
| I | 6 hours<br>6 hours<br>6 hours |
| II | >6 hours<br>~15 minutes<br>~10 minutes<br>~5 minutes |
| III | n.d.<br>~12 minutes |
| IV | n.d.<br>~1 hour |
| V | >6 hours<br>>6 hours |
| VI | >6 hours<br>~15 minutes |

FIGURE 8
SHT. 1 OF 2

FIGURE 8
SHT 2 OF 2

| Construct type | Half-life |
|---|---|
| VII | >6 hou... |
| VIII | ~30 mir... |
| IX | >6 hou... |
| X | ~45 mir... |
|  | >6 hou... |
|  | ~4 hou... |
|  | >6 hou... |
|  | ~3 hou... |
|  | n.d. |
| XI | ~1 hou... |
|  | n.d. |
| XII | >6 hou... |
|  | n.d. ur... |
| XIII | >6 hou... |

METHODS OF GENERATING DESIRED AMINO-TERMINAL RESIDUES IN PROTEINS

RELATED APPLICATIONS

This application is a continuation application Ser. No. 08/239,800, filed May 9, 1994, now U.S. Pat. No. 5,496,721 which is a continuation of application Ser. No. 07/988,807 filed on Dec. 10, 1992 (now abandoned), which is a continuation of application Ser. No. 07/821,720, filed Jan. 15, 1992 (now U.S. Pat. No. 5,196,321), which is a continuation of application Ser. No. 07/356,378, filed May 24, 1989 (now U.S. Pat. No. 5,093,242), which is a continuation-in-part of application Ser. No. 07/178,924, filed Apr. 7, 1988 (now U.S. Pat. No. 5,132,213), which is a continuation-in-part of application Ser. No. 07/103,910, filed Oct. 1, 1987 (now abandoned), which is a continuation-in-part of application Ser. No. 06/915,151, filed Oct. 2, 1986 (now abandoned).

BACKGROUND OF THE INVENTION

In both bacterial and eukaryotic cells, relatively long-lived proteins, whose half-lives are close to or exceed the cell generation time, coexist with proteins whose half-lives can be less than one percent of the cell generation time. Rates of intracellular protein degradation are a function of the cell's physiological state, and appear to be controlled differentially for individual proteins. In particular, damaged and otherwise abnormal proteins are metabolically unstable in vivo. Although the specific functions of selective protein degradation are in most cases still unknown, it is clear that many regulatory proteins are extremely short-lived in vivo. Metabolic instability of such proteins allows for rapid adjustment of their intracellular concentrations through regulated changes in rates of their synthesis or degradation. The few instances in which the metabolic instability of an intracellular protein has been shown to be essential for its function include the cII protein of bacteriophage lambda and the HO endonuclease of the yeast *Saccharomyces cerevisiae*.

Most of the selective turnover of intracellular proteins under normal metabolic conditions is ATP-dependent and (in eukaryotes) nonlysosomal. Recent biochemical and genetic evidence indicates that, in eukaryotes, covalent conjugation of ubiquitin to short-lived intracellular proteins is essential for their selective degradation. The rules which determine whether a given protein is metabolically stable or unstable in vivo were previously unknown.

SUMMARY OF THE INVENTION

This invention pertains to methods of engineering the amino-terminus of proteins thereby controlling the metabolic stability and other properties of a protein. Further, this invention provides a method for either in vivo or in vitro production of proteins with any of the twenty amino acid residues (or analogs thereof) at the protein's amino-terminus. The invention is based in part upon the striking discovery that the in vivo half-life of an intracellular protein is a function of its amino-terminal amino acid residue and upon a novel (and more generally applicable) technique that allows one to generate proteins with specified amino-termini in vivo or in vitro. The invention also pertains to a newly identified protease, ubiquitin-specific processing protease, which has properties that allow one to expose, either in vitro or in vivo, any desired amino acid residue, other than proline, at the amino-terminus of a protein of interest.

The nature of the amino acid exposed at the amino-terminus of an intracellular protein was shown to be one crucial determinant that specifies whether a protein will be long- or short-lived in vivo. Individual amino acids can be categorized as either stabilizing or destabilizing amino acids with respect to the half-life that they confer upon a protein when exposed at the protein's amino-terminus. Destabilizing amino acid residues confer short half-lives, down to a few minutes for some of the destabilizing amino acids. Stabilizing amino acid residues confer long half-lives of many hours. This striking and newly discovered dependency of a protein's half-life on its amino-terminal residue is referred to herein as the N-end rule.

For some proteins, the presence of a destabilizing amino acid at the amino terminus is necessary but not sufficient for destabilization. This is so because the complete amino-terminal degradation signal in a short-lived protein comprises two distinct determinants, each of which is necessary, but each of which, by itself, is insufficient for efficient destabilization of a protein. One determinant, described above, is the amino-terminal residue of the protein. The second determinant, described below, is a specific internal lysine residue. The ability of this critical lysine residue to serve as the second determinant is to a significant extent independent of the amino acid sequences surrounding the residue. Instead, an essential feature of this critical lysine residue includes its spatial proximity to the protein's amino-terminus.

Based upon the N-end rule, the amino-terminus of a protein can thus be designed or altered to change the intracellular half-life of the protein and in this way the lifetime and/or activity of the protein in vivo can be regulated. This capability can be exploited for rational protein design in many different contexts. Natural proteins can be modified to render them more or less resistant to degradation in vivo. The design or alteration of the protein can be done at the protein level or at the genetic (DNA) level. For example, proteins can be modified by chemically altering or engineering the amino-terminus to provide for exposure at the amino-terminus of an amino acid residue of the stabilizing or destabilizing class. At the genetic level, genes encoding proteins can be made to encode an amino acid of the desired class at the amino-terminus so that the expressed protein exhibits a predetermined amino-terminal structure which renders it either metabolically stable or unstable with respect to the N-end rule pathway of proteolytic degradation. Amino-terminal regions can be engineered to provide appropriately located lysine residues in the context of a sufficiently segmentally mobile amino terminus to produce destabilized protein. Furthermore, proteins can be expressed fused to a "masking" protein sequence which masks the engineered amino-terminus so that when unmasked the protein will exhibit the desired metabolic stability or other properties that depend on the nature of the protein's amino-terminal residue. In such constructs, for example, the junction between the two protein sequences can be designed to be cleaved specifically, for instance, by an endoprotease. Endoproteolytic cleavage of the fused sequence unmasks the specifically engineered amino-terminus of the protein of interest and subjects the protein to degradation governed by the N-end rule. One specific and new way to engineer the protein's amino-terminus is provided in this invention by the identification of ubiquitin-specific processing protease and determination of its substrate specificity. Using this protease, fusions of ubiquitin with other proteins can be specifically processed either in vitro or in vivo to generate proteins with desired amino-terminal residues.

A different, and also new way to specifically engineer short-lived proteins is provided in this invention by the discovery that ubiquitin-protein fusions, such as ubiquitin-Pro-β-galactosidase, that cannot be efficiently deubiquitinated, are metabolically unstable. Thus, by attaching the amino-terminal ubiquitin moiety to a protein in a way that makes its removal either impossible or inefficient, one can destabilize proteins by a distinct technique that is not directly based on the N-end rule.

In addition, variant cells can be developed which contain putative mutations in the "N-end" degrading protease(s) which either conditionally or nonconditionally stop degrading short-lived proteins. These cells can be used to overproduce proteins that ordinarily would be short-lived within the cell.

BRIEF DESCRIPTION OF THE FIGURES

FIGS. 3A and 3B show the changing of amino acid residues at the ubiquitin-β-gal junction (A) using the newly discovered properties of ubiquitin-specific processing protease and the amino acid sequence in the vicinity of the junction (B).

FIGS. 7A–7C and 8 show the construction of ubiquitin fusions with mouse dihydrofolate reductase.

DETAILED DESCRIPTION OF THE INVENTION

Figure 1:
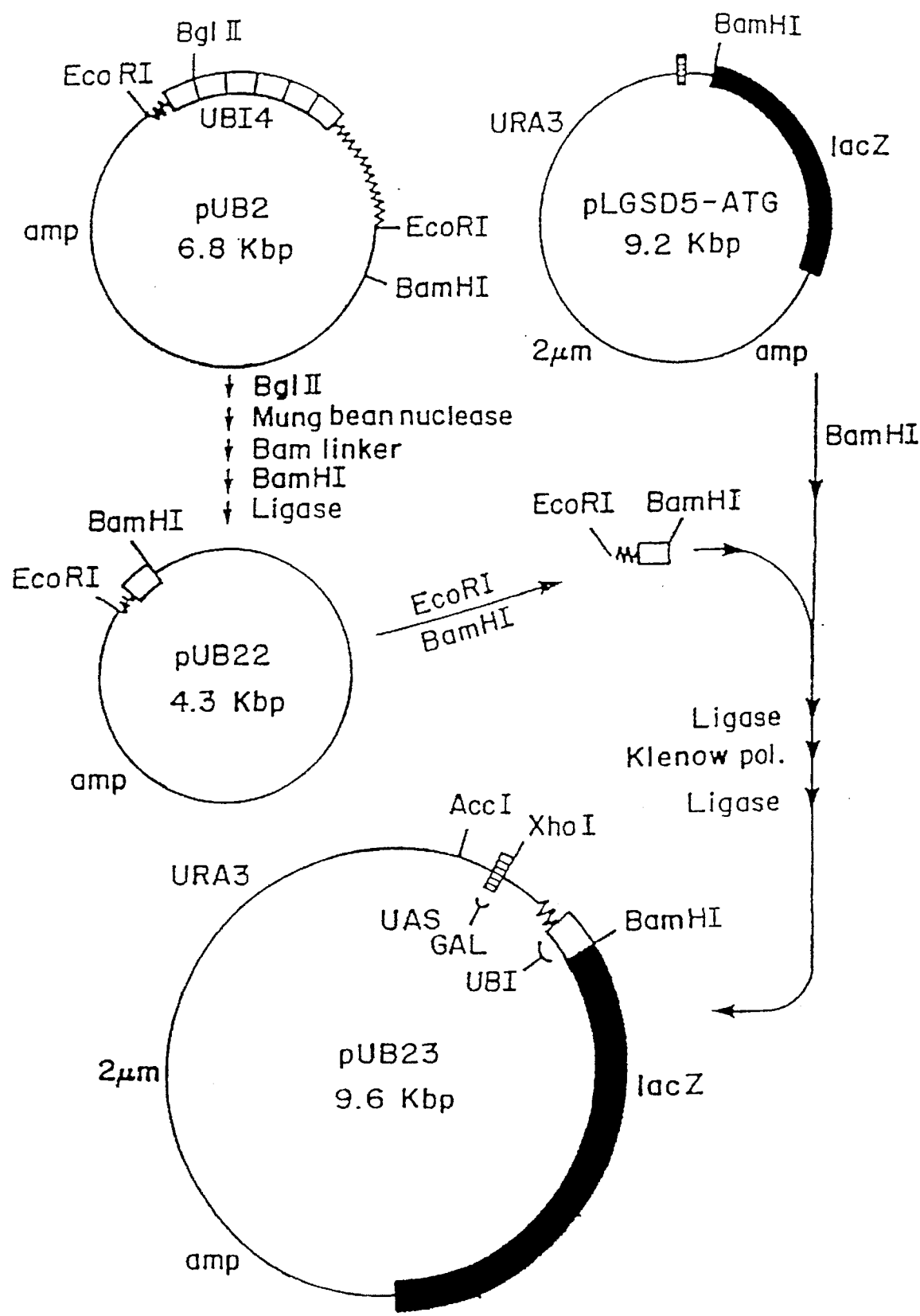
FIG. 1 shows the construction of ubiquitin-lacZ gene fusions.

The elucidation of the N-end rule is described in detail below. Briefly, this rule governing protein degradation was revealed by examining the in vivo half-lives of the enzyme β-galactosidase having various amino acid residues at its amino-terminus and produced as a fusion protein with ubiquitin. When a chimeric gene encoding a ubiquitin-β-galactosidase fusion protein is expressed in the yeast S. cerevisiae, ubiquitin is cleaved off the nascent fusion protein, yielding a deubiquitinated-β-galactosidase (βgal). With one exception, this cleavage takes place efficiently regardless of the nature of the amino acid residue of βgal at the ubiquitin-βgal junction, thereby making it possible to expose selectively different residues at the amino-termini of otherwise identical βgal proteins. The βgal proteins so designed exhibited strikingly different half-lives in vivo, ranging from more than 20 hours to less than 3 minutes, depending upon the nature of amino acid at the amino-terminus of βgal. Amino acids can be thus ordered according to the the half-lives they confer on βgal when present at its amino-terminus. For example, the amino acids methionine, serine, alanine, threonine, valine, glycine and cysteine confer a half-life of more than 20 hours. Phenylalanine, leucine, asparagine, and lysine yield half-lives of about three minutes. Arginine, the most destabilizing amino acid, confers a half-life of about two minutes. (See Table 1 below for complete list of amino acids and the corresponding half-lives)

A similar result is observed when $^{35}S$ labelled proteins are synthesized in E. coli, isolated, and added to a mammalian cell lysate, specifically, the well characterized rabbit reticulocyte lysate system. In such a system, for example the following amino-terminal residues can be characterized as destabilizing: arginine, lysine, histidine, phenylalanine, leucine, tryptophan, tyrosine, alanine, serine, threonine, aspartic acid, glutamic acid, glutamine, cysteine and asparagine. Whether a particular amino acid is destabilizing in any eukaryotic system can be determined.

Through the course of these studies, it has been determined that the N-end rule has a hierarchical structure. Specifically, amino-terminal Glu and Asp (and also Cys in reticulocytes) are secondary destabilizing residues in that they are destabilizing through their ability to be conjugated to primary destabilizing residues such as Arg. Amino-terminal Gln and Asn are tertiary destabilizing residues in that they are destabilizing through their ability to be converted, via selective deamidation, into secondary destabilizing residues Glu and Asp.

Currently known amino-terminal residues in long-lived, noncompartmentalized intracellular proteins from both prokaryotes and eukaryotes belong virtually exclusively to the stabilizing class of amino acids, exactly as predicted by the N-end rule. This result stongly implicates the N-end rule in the selective degradation of intracellular proteins in general.

The appropriate amino-terminal amino acid appears to be an essential (though not necessarily a sufficient) requirement for the metabolic stability of a noncompartmentalized, intracellular protein. Thus, in order for a protein to be relatively stable intracellularly, a stabilizing amino acid should be present at the amino-terminus. The presence of a destabilizing residue at the amino-terminus of a protein is often, though not always, sufficient for its metabolic destabilization in vivo. When such destabilization occurs to a relatively small extent, further analysis shows either an insufficient accessibility of the amino-terminus or a lack of the second determinant of the complete amino-terminal degradation signal. In these instances, this second determinant, which by itself does not metabolically destabilize a protein, must be present in order for the half-life of a protein in vivo to be strongly dependent on the nature of its amino-terminal residue. The second determinant of the amino-terminal degradation signal was found to be a specific internal lysine residue. The ability of this critical lysine residue to serve as the second determinant was shown to be largely independent of unique amino acid sequences surrounding the residue. Instead, an essential features of the critical lysine residue includes its spatial proximity to the protein's amino-terminus.

The presence of a stabilizing amino acid at the amino-terminus at least in some cases (for instance, as observed for β-gal) will confer stability upon the protein. However, a stabilizing amino acid at the amino-terminus may not always confer a long half-life because other degradative pathways may be involved in determining the ultimate fate of the protein. For example, endoproteolytic cleavages (cleavages outside of terminal regions of the protein) may result in exposure of a destabilizing amino acid at the amino-terminus of a resulting product of the cleavage which is then rapidly degraded via the N-end rule pathway. Appropriate circumstances for use of a stabilizing amino acid can be ascertained empirically.

Although the N-end rule may be only one component (albeit a central one) of a more complex "half-life rule" which embraces other aspects of selective protein degradation in vivo, the N-end rule provides a rational, practical approach for designing or changing protein structure in order to produce proteins which are more or less resistant to degradation by the N-end rule pathway than natural, unmodified protein. Proteins can be designed or modified at the protein or gene level to provide a desired amino acid of either the stabilizing or destabilizing class at their amino-terminus. Where necessary for destabilization, additional modifications can be made to the amino-terminal region to provide appropriately located lysine residues. The ability to regulate the half-life of a protein will allow one to modulate the intracellular activity of the protein.

A straightforward approach to modifying a protein in order to increase or decrease its metabolic stability or to modulate other properties of the protein is to directly engineer the amino-terminus of the protein at the protein level. To provide a desired amino-terminal amino acid, the amino-terminus of the protein of interest can be chemically altered, for example, by adding an amino acid of the stabilizing or destabilizing class to the amino-terminus of a protein or polypeptide, employing an appropriate chemistry. Thus, for example, an unstable protein can be rendered more stable by adding a stabilizing amino acid residue (e.g. methionine serine, alanine, threonine, valine glycine or cysteine) to the amino-terminus of the protein. Conversely, a stable protein can be destabilized by adding a destabilizing amino acid to the amino-terminus. One distinct way to modify the amino-terminus of a protein would be to employ specific enzymes, amino acid-protein ligases, which catalyze posttranslational addition of a single amino acid to the protein's amino-terminus. Other methods for nongenetic alterations of the same type can readily be ascertained by those skilled in the art.

In some proteins, the amino-terminal end is obscured as a result of the protein's conformation (i.e., its tertiary or quaternary structure). In these cases, more extensive alteration of the amino-terminus may be necessary to make the protein subject to the N-end rule pathway. For example, where simple addition or replacement of the single amino-terminal residue is insufficient because of an inaccessible amino-terminus, several amino acids (including lysine, the site of ubiquitin joining to substrate proteins) may be added to the original amino-terminus to increase the accessibility and/or segmental mobility of the engineered amino terminus.

Modification or design of the amino-terminus of a protein can also be accomplished at the genetic level. Conventional techniques of site-directed mutagenesis for addition or substitution of appropriate codons to the 5' end of an isolated or synthesized gene can be employed to provide a desired amino-terminal structure for the encoded protein. For example, so that the protein expressed has the desired amino acid at its amino-terminus the appropriate codon for a stabilizing amino acid can be inserted or built into the amino-terminus of the protein-encoding sequence. Where necessary, the DNA sequence encoding the amino-terminal region of a protein can be modified to introduce a lysine residue in an appropriate context. This can be achieved most conveniently by employing DNA constructs encoding "universal destabilizing segments". A universal destabilizing segment comprises a DNA construct which encodes a polypeptide structure, preferably segmentally mobile, containing one or more lysine residues, the codons for lysine residues being positioned within the construct such that when the construct is inserted into the structural gene, the lysine residues are sufficiently spatially proximate to the amino-terminus of the encoded protein to serve as the second determinant of the complete amino-terminal degradation signal. An example of a destabilizing segment is shown in the exemplification below (see FIGS. 7 and 8). The insertion of such constructs into the 5' portion of a structural gene would provide the encoded protein with a lysine residue (or residues) in an appropriate context for destabilization.

At the same time, expressed proteins are often naturally modified within a cell after translation. These modifications can include changes at the protein's amino-terminus. For example, the amino-terminus can be acted on by an aminopeptidase which cleaves one or several amino acids from the amino-terminus. Amino acids may also be added to the amino-terminus by post-translational processing. This invention provides a way to "by-pass" still undefined rules of amino-terminal protein processing to expose exactly and specifically the desired amino acid residues at the amino-terminus of a mature processed protein species. To minimize the impact of such posttranslational events on the ultimate structure of the amino-terminus of a protein of interest, specific fusion proteins can be designed wherein the amino-terminus of a protein of interest (designed to have the desired stabilizing or destabilizing structure) is preceded by a "masking" protein sequence fused to the amino-terminus. The fusion proteins are designed so that the masking protein sequence fused to the amino-terminus of the protein of interest is susceptible to specific cleavage at the junction between the two. Removal of the protein sequence thus unmasks the amino-terminus of the protein of interest and the half-life of the released protein is thus governed by the predesigned amino-terminus. The fusion protein can be designed for specific cleavage in vivo, for example, by a host cell endoprotease or for specific cleavage in a in vitro system where it can be cleaved after isolation from a producer cell (which lacks the capability to cleave the fusion protein).

Ubiquitin is a broadly useful fusion partner for construction of a fused protein with a protein of interest: the discovery that artificial ubiquitin-protein fusions can be cleaved precisely by a cytoplasmic eukaryotic protease with little or no dependence on the protein to which ubiquitin is fused can be applied both in vivo and in vitro in protein engineering strategies, and is a major aspect of this invention. For example, the ubiquitin-protein fusion method can be used artificially generate authentic amino-termini in proteins produced through artificial means. Thus, amino-termini characteristic of natural eukaryotic or prokaryotic proteins can be generated by in vitro cleavage of ubiquitin-protein fusions produced in a prokaryotic host.

A specific methodology for producing ubiquitin-β-galactosidase fusion proteins is described in detail below. Genes encoding any other proteins can be substituted for LacZ (the β-gal gene) in this methodology.

In general, ubiquitin fusion proteins are expressed by a chimeric gene construct comprising, in 5' to 3' orientation, a ubiquitin gene linked to a gene encoding the protein of interest. The codon for the amino-terminal amino acid of the protein of interest is located immediately adjacent the 3' end of the ubiquitin gene. The fused gene product is cleaved endoproteolytically either in vivo or in vitro (using either pure or partially purified ubiquitin-specific protease identified in the present invention) at the junction between ubiquitin and the protein of interest to generate the protein of interest having the desired amino acid at its amino-terminus.

There are a number of specific uses for the described ability to specifically engineer the protein's amino-terminus. One such use is established by the fact that the intracellular half-life of the released protein is governed by the principles of the N-end rule. Other applications of the specific method for engineering the protein's amino-terminus described herein range from adjusting the desired functional properties of a protein of interest, to modulating its antigenicity, and again, to other uses that can readily be ascertained by those skilled in the art.

This method of generating the desired amino acid residue at the amino-terminus of a protein of interest involves two novel components: one, the use of ubiquitin-protein fusions, and the other, the use of ubiquitin-specific processing protease that has been identified, and whose striking substrate requirements were discovered, in this work. Although the initial identification of the ubiquitin-specific protease has been made in vivo, the enzyme is also relatively stable and active in vitro (in extracts), and can readily be purified to homogeneity by techniques known to those skilled in the art. Furthermore, the substrate specificity of the ubiquitin-specific processing protease is highly conserved in evolution, being the same in yeast and mammals. The enzyme can be purified chromato-graphically from a crude extract by sequential chromatography on phosphocellulose, DEAE cellulose, and SH-Sepharose among other methods known to those skilled in the art. Alternatively, the gene for this protease can be cloned by those skilled in the art.

The cloned protease gene can be used either in vivo, or, alternatively, the gene can be over-expressed in a suitable host, the overexpressed ubiquitin-specific protease purified and used for the same or similar purposes in vitro. The discovery of this enzymatic activity, and detailed characterization of its substrate specificity herein provides for the in vitro and in vivo use of this enzyme.

The use of ubiquitin-protein fusions to allow the generation of a desired amino acid residue at the amino-terminus of a protein of interest can be extended to facilitate the purification of such proteins from producer cells. A gene can be readily constructed that encodes a convenient marker protein, such as streptavidin, linked to a ubiquitin-protein fusion construct described above. The resulting (marker protein)-ubiquitin-protein fusion can be simply isolated from producer cells by using the preselected property of the marker protein, for instance, the known ability of streptavidin to be isolatable by affinity chromatography on a biotin column. Thus, purified (marker protein)-ubiquitin-protein fusion can then be specifically cleaved by the ubiquitin-specific protease described in this invention to generate the final product, a protein of interest with the desired amino acid residue at its amino-terminus.

The codon for the amino-terminal amino acid of the protein of interest can be made to encode the desired amino acid by, for example, site-directed mutagenesis techniques currently standard in the field. If the gene encoding the protein of interest is a synthetic gene the appropriate 5' codon can be built-in during the synthetic process. Alternatively, nucleotides for a specific codon can be added to the 5' end of an isolated or synthesized gene by ligation of an appropriate DNA sequence to the 5' (amino-terminus-encoding) end of the gene. DNA inserts encoding appropriately located lysine residues (such as the "universal destabilizing segments" described above) can be inserted into the 5' region to provide for the second determinant of the complete amino-terminal degradation.

Ubiquitin-like fusion partners capable of being cleaved by the ubiquitin-specific protease can also be used. In addition, fusion partners other than ubiquitin for masking the amino-terminus of a protein of interest can be used. For example, functional homologues of ubiquitin from eukaryotes or prokaryotes may be used. In appropriate cases, the fusion proteins can be designed to contain a proteolytic cleavage site for a restriction endoprotease which has sufficiently narrow specificity so that only one target site is cleaved in a fusion protein. A crucial property of such a protease must be a sufficiently relaxed requirement for the nature of the amino acid residue(s) abutting the carboxy-terminal side of the cleavage site. The target site for cleavage is the junction between the fusion partner and the amino-terminus of the protein of interest and thus the recognition site for the endoprotease is located to provide for cleavage at this location. The commerically available protease, complement factor $X_a$ exhibits these properties and thus can be used to directly generate proteins with predetermined amino acid residues in the ultimate position of their amino-termini (see, K. Nogai and H. C. Thogersen Nature 309:810 (1984)). The recognition site for the endoprotease can be engineered into the junction between the masking protein sequence and the 3' region encoding the amino-terminus of the protein of interest.

A different and distinct method for engineering short-lived proteins is provided in this invention by the discovery that ubiquitin-protein fusions, such as ubiquitin-Pro-β-galactosidase fusion (Table 1), that cannot be efficiently deubiquitinated are metabolically unstable. Thus, by attaching the amino-terminal ubiquitin moiety to a protein in a way that makes its removal either impossible or inefficient, one can destabilize a protein by a distinct technique which is qualitatively different from the method of generating the desired amino-terminus of a protein according to the requirements of the N-end rule. Prevention of the efficient deubiquitination of a ubiquitin-protein fusion can be achieved in several ways, for instance, by using a proline residue at the ubiquitin-protein junction as shown in Table 1, or by changing the amino acid sequence of ubiquitin near its carboxyl-terminus in such as way that the ubiquitin moiety is no longer recognized by the ubiquitin-specific processing protease but can still be recognized by the rest of the degradative pathway. These and other ways to reduce the rate of deubiquitination of a ubiquitin-protein fusion can be readily ascertained by those skilled in the art.

The methods of this invention can be employed, inter alia, for regulating the half-life of a protein intracellularly. There are many instances where this capability is useful. For example, when a gene is introduced into a cell for expression therein, the expressed product can be designed for a long or short half-life depending upon the particular need.

In general, destabilized proteins which have short half-lives are more amenable to regulation of intracellular levels of the protein. The ability to finely regulate the intracellular levels and activity of a protein can be useful in therapy or in the work with in vitro cell cultures. In gene therapy, for example, a gene may be introduced into a cell to compensate for a genetic deficiency or abnormality. The gene can be inserted under control of an inducible promoter. Induction results in enhanced expression of the gene product and consequently, higher levels of the product within the cell. If the gene is designed to encode an unstable protein, the intracellular concentration of the expressed protein will be more quickly responsive a later reduction in the rate of its synthesis because it does not persist within the cell. In this way, the intracellular level and/or activity of the protein encoded by the inserted gene can be more finely regulated.

The method of this invention can also be used to expand the uses of selectable markers by shortening the time necessary for a phenotype related to the marker to become manifest. Toward this end, a product encoded by a marker gene can be destabilized by altering its amino-terminus according to the N-end rule. In this way selection for the negative phenotype can be facilitated because the product of the marker gene will be more quickly extinguished after the function of the gene encoding the marker is abolished. An example is the thymidine kinase (tk) gene. The tk gene can be engineered to encode a less stable enzyme by introducing an appropriate destabilizing amino acid at the amino-terminus. Gene mutation resulting in tk⁻ phenotype will be more quickly manifested by cells because residual tk will be more quickly degraded. This can be especially useful in slow growing cells where more time is required to "dilute out" tk synthesized prior to transformation to the tk⁻ type.

The principles of protein modification based upon the N-end rule may also be employed in the design of cytotoxins. Proteinaceous cytotoxins can be designed as unstable proteins degradable by the N-end rule pathway so that they do not persist after their toxic action has been exerted on a target cell. Reducing the lifetime of the toxin reduces the likelihood of killing nontargeted cells.

Discovery of the N-end rule pathway of degradation allows development of mutant cells having mutations in genes encoding essential components of the N-end rule pathway. For example, cells can be produced that either permanently or conditionally are unable to efficiently degrade otherwise short-lived proteins. These cells can be used to produce desired proteins that ordinarily would be unstable within a cell.

The invention is illustrated further by the following detailed description of the elucidation of the N-end rule.

Methods

Protein Sequencing

*S. cerevisiae* cells carrying pUB23 (FIG. 1), which encodes ub-Met-βgal (FIG. 3A), were labeled with [$^{35}$S] methionine, followed by extract preparation, immunoprecipitation of βgal and electrophoresis as described below. The wet polyacrylamide gel was subjected to autoradiography, the band of βgal was excised, and the electroeluted βgal was subjected to six cycles of radiochemical sequencing by Edman degradation. The sequencing was carried out by W. Lane at the MicroChem Facility of Harvard University.

Site-directed Mutagenesis pUB23 (FIG. 1) was treated sequentially with Acc I, the Klenow fragment of pol I, and Bam HI. A fragment containing the Xho I site was purified and inserted between a filled-in Hind III site and a BAH HI site of the M13mp9 phage DNA. (J. Messing and J. Vieira, *Gene* 19, 263 (1982)). Site-directed mutagenesis (M. Smith, *Annu. Rev. Genet.* 19, 423 (1985)) was carried out as described by Kramer, W. et al. *Nucl. Acids Res.* 12, 9441 (1984) using a synthetic 25-residue oligodeoxyribonucleotide, containing ten bases on the 5' side and twelve bases on the 3' side of the Met codon of gal. All four bases were allowed to occur at the original Met codon positions during synthesis. Primary phage plaques were screened by hybridization (Wood, N. I. et al. PNAS 82, 1585 (1985)), with the use of a 12-residue oligonucleotide probe spanning the region of codon changes and hybridizing to the original sequence. Nonhybridizing plaques containing inserts of the expected size were sequenced by the chain termination method. (Sanger, F. et al., *PNAS* 71 5463 (1977)). To transfer the desired constructs into the pUB23 background, replicative form DNA of mutant phages was digested with Xho I and Bam HI, and added to the same digest of the plasmid pLGSD5-ATG (see FIG. 1 and L. Guarente, *Methods Enzymol.*, 101 181 (1983) ). The ligated mixture was used to transform the *E. coli* strain MC1061. (M. J. Casadaban and S. N. Cohen, *J. Mol. Biol.*, 138 179 (1980)). Colonies containing plasmids of interest (in which the open reading frame of βgal had been restored) were recognized by their light blue color on X-βgal plates.

Pulse-Chase Experiments

*S. cerevisiae* cells of the strain BWG-9a-1 (MAT his4 ura3 ade6), transformed (F. Sherman et al. *Methods in Yeast Genetics* Cold Spring Harbor Laboratory, N.Y., 1981)) with plasmids of interest were grown at 30° C. to $A_{600}$ of approximately 5 in a medium of 2 percent galactose, 0.67 percent Yeast Nitrogen Base without amino acids (DIFCO), adenine (10 µg/ml) and amino acids including methionine (Sherman, F. et al., supra). Typically, cells from a 5 ml culture were harvested by filtration through the well of a Millipore nicrotiter filtration plate, washed several times on the filter with the same medium lacking methionine and resuspended in 0.3 ml of 1 percent galactose, 50 mM potassium phosphate buffer (pH 7.4). [$^{35}$S]methionine (50 to 100 µCi) was then added for 5 minutes at 30° C.; the cells were collected by filtration and resuspended on 0.4 ml of the growth medium containing cycloheximide at 0.5 mg/ml. Samples (0.1 ml) were withdrawn at indicated times, and added to 0.75 ml of cold buffer A (see below for buffer composition) containing leupeptin, pepstatin A, antipain, aprotinin and chymostatin (Sigma), (each at 20 µg/ml) in addition to 0.4 ml of glass beads. Immediately thereafter, the cells were disrupted by vortexing for approximately 3 minutes at 4° C.; the extracts were centrifuged at 12,000 g for 3 minutes and the radioactivity of acid-insoluble $^{35}$S in the supernatants was determined. Aliquots of the supernatants containing equal amounts of the total acid-insoluble $^{35}$S were processed for immuno-precipitation with a monoclonal antibody to βgal. Ascitic fluid containing a molar excess of the antibody (at least tenfold) was added to each aliquot, with subsequent incubation at 4° C. for 2 hours; protein A-Sepharose (Pharmacia) was then added, the suspension was incubated with rocking at 4° C. for 30 minutes and centrifuged at 12,000 g for 1 minute. The protein A-Sepharose pellets were washed three times in buffer A (see below) containing 0.1 percent sodium dodecyl sulfate (SDS), resuspended in an SDS, dithiotreitol (DTT)-containing electro-phoretic sample buffer (U. K. Laemmli, *Nature* 227 680 (1970)), heated at 100° C. for 3 minutes, and centrifuged at 12,000 g for 1 minute. Equal aliquots of the supernatants were subjected to electrophoresis in a 7 percent discontinuous polyacrylamide-SDS gel (15 by 15 by 0.15 cm) with subsequent flourography. In some experiments, the above protocol was not used, but the extracts were prepared by boiling cells directly in the presence of SDS, with essentially the same results.

Analysis of ub-βgal proteins produced in *E. Coli*

Plasmid pUB23 (FIGS. 1 and 3) was introduced into DS410, a minicell-producing *E. coli* strain. (N. Stoker, et al., in *Transcription and Translation: A practical Approach* B. D. Harnes and S. J. Higgins, Eds., IRL press, Oxford, 1984, p. 153). Minicells were prepared and labeled for 60 minutes at 36° C. with [$^{35}$S]methionine (600 Ci/mmole, Amersham) as described by N. Stoker et al., supra.

Labeled minicells were centrifuged, resuspended in 2 percent SDS, 10 mM DTT, 10 mM Na-HEPES (ph 7.5) and heated at 100° C. for 3 minutes. After centrifugation at 12,000 g for 1 minute the supernatant was diluted 20-fold with buffer A (1 percent Triton X-100, 0.15M NaCl, 5 mM Na-EDTA, 50 mM Na-HEPES, pH 7.5), followed by the addition of phenylmethylsulfonyl fluoride (PMSF) and N-ethylmaleimide to 0.5 mM and 10 mM, respectively. After 4 hours at 4° C., the sample was dialyzed against buffer A containing 0.5 mM PMSF overnight at 4° C., and processed for immunoprecipitation (as described above).

Analysis of ub-βgal proteins produced in yeast

S. cerevisiae cells carrying plasmids of interest were grown in 800 ml of a uracil-deficient medium, then harvested and disrupted with glass beads in buffer A containing leupeptin, pepstatin A, antipain, aprotinin and chymostatin (each at 3 µg/ml). The extract was centrifuged at 12,000 g for 3 minutes. Saturated ammonium sulfate was added to the supernatant to a final concentration of 57 percent. After overnight incubation at 4° C., the precipitated protein was collected by centrifugation at 23,000 g for 30 minutes. The pellet was redissolved in buffer A containing protease inhibitors. After clarification at 12,000 g for 3 minutes, the sample was passed through an affinity column which had been prepared by crosslinking an IgG fraction from an ascitic fluid (containing a monoclonal antibody to gal to Affi-Gel 10 (Bio-Rad). The IgG fraction used for crosslinking had been purified from the ascitic fluid by affinity chromatography on protein A-Sepharose. After washing with buffer A lacking Triton X-100, the antibody-bound proteins were eluted with 0.25M glycine-HCl (pH 2.6). The eluate was immediately adjusted to pH 7.5 with 1M Na-HEPES (pH 8.5), and thereafter made 0.1 percent in SDS. The sample was concentrated by ultrafiltration in Centricon 30 (Amicon), and subjected to electrophoresis in a 7 percent discontinuous polyacrylamide-SDS gel (U. K. Laemmli, Nature (London) 227, 680 (1970)). Electroblotting of proteins to nitrocellulose, and immunoblot analysis with a peptide-mediated antibody to ubiquitin were performed as described by P. S. Swerdlow, D. Finley and A. Varshavsky, Analyt. Biochem. 156, 147 (1986). The same results were obtained with a different antibody to ubiquitin obtained from A. Haas (Univ of Milwaukee Med. School).

Construction of E. coli Expression Vectors Encoding Twenty Ub-X-βgal Fusion Proteins Four of the pKKUb-X-βgal vectors (those encoding Ub-MET-βgal, Ub-Gln-βgal, Ub-Arg-βgal, and Ub-Pro-βgal) were constructed as follows. Site-directed mutagenesis [M. Smith, Annu. Rev. Genet. 19, 423 (1985); T. Maniatis, et al., "Molecular Cloning", (Cold Spring Harbor Laboratory, N.Y., 1982); "Current Protocols in Molecular Biology", F. M. Ausubel, et al., (Wiley-Interscience, N.Y., 1987] was used to insert the sequence GTAC between the first and second codons of the ubiquitin reading frame in the yeast expression vector pUB23 (which encodes Ub-Met-βgal) and in its derivatives, (A. Bachmair, et al., Science 234, 179 (1986), encoding Ub-Arg-βgal, Ub-Gln-βgal, and Ub-Pro-βgal. The insertion created a Kpn I site positioned such that when the vector is cut with Kpn I and the ends blunted by mung bean nuclease, the second codon of the ubiquitin reading frame starts precisely at one of the fragment's ends. Thus, digestion of each of the above four vectors with Kpn I and Tth 111I, followed by treatment with mung bean nuclease, yielded four fragments which contained the corresponding Ub-X-βgal-coding sequences but lacked the first (ATG) codon of the ubiquitin reading frame. These fragments were subcloned into an E. coli expression vector pKK233-2 [E. Amann and J. Brosius, Gene 40, 183 (1985)] which had been prepared by digesting it with Nco I and filling in staggered ends using Klenow fragment of Pol I [M. Smith, Annu. Rev. Genet. 19, 423 (1985); T. Maniatis, et al., "Molecular Cloning", (Cold Spring Harbor Laboratory, N.Y., 1982); "Current Protocols in Molecular Biology", F. M. Ausubel, et al., (Wiley-Interscience, N.Y., 1987)]. This step yielded the complete Ub-X-βgal sequence (in which the ATG codon was supplied by the pKK233-3 vector), optimally positioned downstream of the regulatable Ptrc promotor of the vector. To construct the remaining sixteen pKKUb-X-βgal expression vectors, pKKUb-Arg-βgal was digested with SalI and BamHI. One of the two BamHI sites in pKKUb-Arg-βgal is located at the junction between the ubiquitin- and βgal-coding sequences; the other BamHI site, present in the initial pKK233-2 vector [E. Amann and J. Brosius, Gene 40, 183 (1985)], was removed in a preliminary construction step. The small SalI/BamHI fragment (containing the Ptrc promoter, the complete ubiquitin-coding sequence, and the Arg codon at the Ub-βgal junction) was subcloned into a M13mp9 vector [M. Smith, Annu. Rev. Genet. 19, 423 (1985); T. Maniatis, et al., "Molecular Cloning", (Cold Spring Harbor Laboratory, N.Y., 1982); "Current Protocols in Molecular Biology", F. M. Ausubel, et al., (Wiley-Interscience, N.Y., (1987); J. Messing and J. Vieira, Gene 19, 263 (1982)]. A BstXI/BamHI fragment of this construct that contained a portion of the ubiquitin-coding sequence and the Arg codon at the Ub-βgal junction, was then exchanged for the sixteen otherwise identical BstXI/BamHI fragments [from the previously made, M13mp9-based constructs A. Bachmair et al., Science 234, 179 (1986)], which differed exclusively in a codon at the Ub-βgal junction. The resulting sixteen M13-mp9-based constructs were treated with SalI and BamHI, and the small SalI/BamHI fragments containing the ubiquitin-coding sequence and different single codons at the Ub-βgal junction were cloned back into pKKUb-Arg-βgal, replacing the original SalI/BamHI fragment, and yielding the remaining sixteen pKKUb-X-βgal expression vectors. In all cases, the identity of the amino acid encoded at the Ub-βgal junction of a final pKKUb-X-βconstruct was verified by subcloning into M13 and nucleotide sequencing by the chain termination method [M. Smith, Annu. Rev. Genet. 19, 423 (1985); T. Maniatis, et al., "Molecular Cloning", (Cold Spring Harbor Laboratory, N.Y., 1982); "Current Protocols in Molecular Biology", F. M. Ausubel, et al., (Wiley-Interscience, N.Y., (1987)].

Purification of $^{35}$S Labeled Ub-X-βgal Proteins From E. coli

An overnight culture (1ml) of E. coli JM101 cells bearing one of the twenty pKKUb-X-βgal expression vectors was diluted into 50 ml of Luria broth supplemented with ampicillin at 40 µg/ml, and the cells were grown with shaking for approximately 2 hours at 37° C. The cells were harvested by centrifugation at 4,000 g for 10 minutes, washed twice with M9 buffer, and resuspended in 25 ml of M9 minimal medium supplemented with glucose (0.22%, w/v), thiamine (18 µg/ml), ampicillin (40 µg/ml), 0.5 mM isopropylthiogalactoside (IPTG), and 0.15 ml of 0.5 % (w/v) Methionine Assay Medium (Difco). After incubation with shaking for one hour at 37° C., 0.5 to 1.0 MCi of $^{35}$S-Translabel (ICN:~85% [$^{35}$S] methionine, ~15% [$^{35}$S] cysteine) was added and shaking was continued for 5 minutes. Unlabeled L-methionine was than added to 1 mM and shaking was continued for another 10 minutes. Cells were harvested, washed twice with M9 buffer, and resuspended in 0.5 ml of 25% (w/v) sucrose, 50 mM Tris-HCl (pH8.0). Thereafter, 0.1 ml of lysozyme (10 mg/ml, Sigma) in 0.25M Tris-HCl (pH 8.0) was added, and the mixture was incubated at 0° C. for five minutes, followed by the addition of 0.1 ml of 0.5M Na-EDTA (pH 8.0) and further incubation at 0° C. for five minutes. The cell suspension was then added to a lysis solution (0.8 ml H$_2$O, 50 µl of 1M Tris-Hcl (pH 8.0), 125 µl of 0.5M Na-EDTA (pH 8.0), 10 µl of 10% (w/v) Triton X-100), and gently mixed. The lysate was centrifuged at 40,000 g for one hour, and Ub-X-βgal was purified from the supernatant by affinity chromatography on an aminophenylthio-pyranogalactoside-agarose (APTG-agarose) column as described (A. Ullman, *Gene* 29, 27 (1984). Ubiquitin-X-βgal was eluted from APTG-agarose with 10 mM 2-mercaptoethanol, 0.1M Na-borate (pH 10.0), dialyzed overnight at 4° C. against 50% (v/v) glycerol, 0.1 mM EDTA, 1 mM dithiothreitol (DTT), 40 mM Tris-HCl (pH 7.5), and stored at –20° C. in the same buffer. Control experiments showed that the transient exposure of Ub-X-βgal purified by the above procedure were 0.5 1 mg, with enzymatic activity of 4–6×10$^4$ units/mg and specific radio-activity of 1–2×10$^5$. Unlabeled Ub-X-βgal was prepared essentially as described above except that after two hours of growth in Luria broth with ampicillin, IPTG was added to 0.5 mM, and the cells were grown for one more hour before harvesting and lysis.

Preparation of Reticulocyte Lysate and Assay for Degradation of Test Proteins

Washed reticulocytes from phenylhydrazine-treated rabbits were purchased from Green Hectares (Oregon, Wisconsin), and shipped overnight at 0° C. The reticulocytes were washed three times with 3–4 volumes of standard phosphate-buffered saline (PBS) (centrifugations at 1000 g for 10 minutes at 4° C.). To deplete intracellular ATP [J. Etlinger and A. Goldberg, *Proc. Natl. Acad. Sci. USA*, 74, 54 (1977); A. Hershko, et al., *Proc. Natl. Acad. Sci. USA* 77: 1783 (1980); Hershko et al., *J. Biol. Chem.*, 258, 8206 (1982)], the cells were incubated for 90 minutes at 37° C. in Krebs-Ringer phosphate buffer containing 0.2 mM 2,4-dinitrophenol and 20 mM 2-deoxyglucose, and then washed three times in PBS. Pelleted reticulocytes were then lysed at 0° C. by resuspending the pellet in 1.5 volumes of 1 mM DTT. After ~10 minutes at 0° C., the sample was centrifuges at 80,000 g for 90 minutes at 4° C. The supernatant was removed, divided into aliquots, and stored under liquid nitrogen. Only once-frozen aliquots were used in all experiments. Unless stated otherwise, the ATP-depleted reticulocyte extract was used directly after thawing, without further processing. In some experiments, the thawed extract was at first dialysed overnight at 4° C. against 1 mM DTT, 10 mM Tris-HCl (pH 7.5) in dialysis tubing with a m.w. cutoff of ~3 kD. Fraction II was prepared by DEAE chromatography of ATP-depleted reticulocyte extract as previously described [D. Finley and A. Varshavsky, *Trends Biochem. Sci.* 10, 343 (1985); A. Herschko and A. Ciechanover, *Progr. Nucl. Ac. Res. Mol. Biol.* 33, 19 (1986); S. Pontremoli and E. Meloni, *Annu. Rev. Biochem.* 55, 455 (1986); M Rechsteiner, *Annu. Rev. Cell. Biol.* 3, 1 (1987); J. S. Bond and P. E. Butler, *Annu. Rev. Biochem.* 56, 333 (1987); J. F. Dice, *FASEB J.* 1, 349 (1987); J. Etlinger and A. Goldberg, *Proc. Natl. Acad. Sci. USA*, 74, 54 (1977); A. Hershko, et al., *Proc. Natl. Acad. Sci. USA* 77: 1783 (1980); Hershko et al., *J. Biol. Chem.*, 258, 8206 (1982)] and stored under liquid nitrogen. Reaction mixtures for assaying the degradation of test proteins in either the total reticulocyte extract of Fraction II contained (final concentrations) 5% (v/v) glycerol, 1 mM DTT, 5 mM MgCl$_2$, 50 mM Tris-HCl (pH 7.5), 70% (v/v) reticulocyte extract (or Fraction II at 6 mg/ml of the total protein), [$^{35}$S]Ub-X-βgal fusion protein at 20 βg/ml, and when present, 0.5 mM ATP and an ATP-regenerating system (10 mM creating phosphate, 0.1 mg/ml creatine phosphokinase). Reaction mixtures were prepared as follows: a mixture complete except for ATP and ATP-regenerating system was incubated for ten minutes at 37° C.; to allow for the deubiquitination of a Ub-X-βgal fusion protein ATP and ATP-regenerating system were then added to start the ATP-dependent reactions in the extract and the 37° C. incubation continued. Control reactions with the ATP-depleted extract were performed identically except that ATP and ATP-regenerating system were omitted. The ATP-dependent degradation of $^{125}$I-labeled bovine serum albumin, hen lysozyme, and cytochrome c from *S. cerevisiae* (purchased from Sigma, St. Louis, Mo., and labeled using the chloramine T method (A. Ciechanover, et al., *Proc. Natl. Acad. Sci. USA* 77, 1365 (1980) was assayed as described above except that the 10-minute preincubation of the test protein at 37° C. in the ATP-depleted reticulocyte extract was omitted. To follow the degradation of test proteins, aliquots were taken from the reaction mixture at the indicated times, and either assayed for the amount of 5% TCA-soluble radioactivity present, or analyzed by SDS-PAGE [U. K. Laemuli, *Nature* 227: 680 (1970)] (8% polyacrylamide, 0.05 bisacrylamide, 15×15×0.15 cm gels), with subsequent fluorography.

Detailed Description of the Figures

FIG. 1 shows construction of a ubiquitin-lacZ gene fusion. pUB2, a pBR322-based genomic DNA clone (E. Ozkaynak, et al. *Nature* 312, 663 (1984) contains six repeats of the yeast ubiquitin-coding sequence (open boxes) together with the flanking regions (jagged lines). pUB2 was modified as shown in the diagram by placing a Bam HI site six bases downstream from the first ubiquitin repeat. This allowed the construction of an in-frame fusion (confirmed by nucleotide sequencing) between a single ubiquitin repeat and the lacZ gene of the expression vector pLGSD5-ATG (called G2 in L. Guarente, *Methods Enzymol.* 101 181 (1983)). The term "2 µm" denotes a region of the pLGSD-ATG that contains the replication origin and flanking sequences of the yeast plasmid called 2 µm circle (See L. Guarente, supra). FIG. 3B shows the amino acid sequence of the fusion protein in the vicinity of the ubiquitin-βgal junction.

Figure 2:
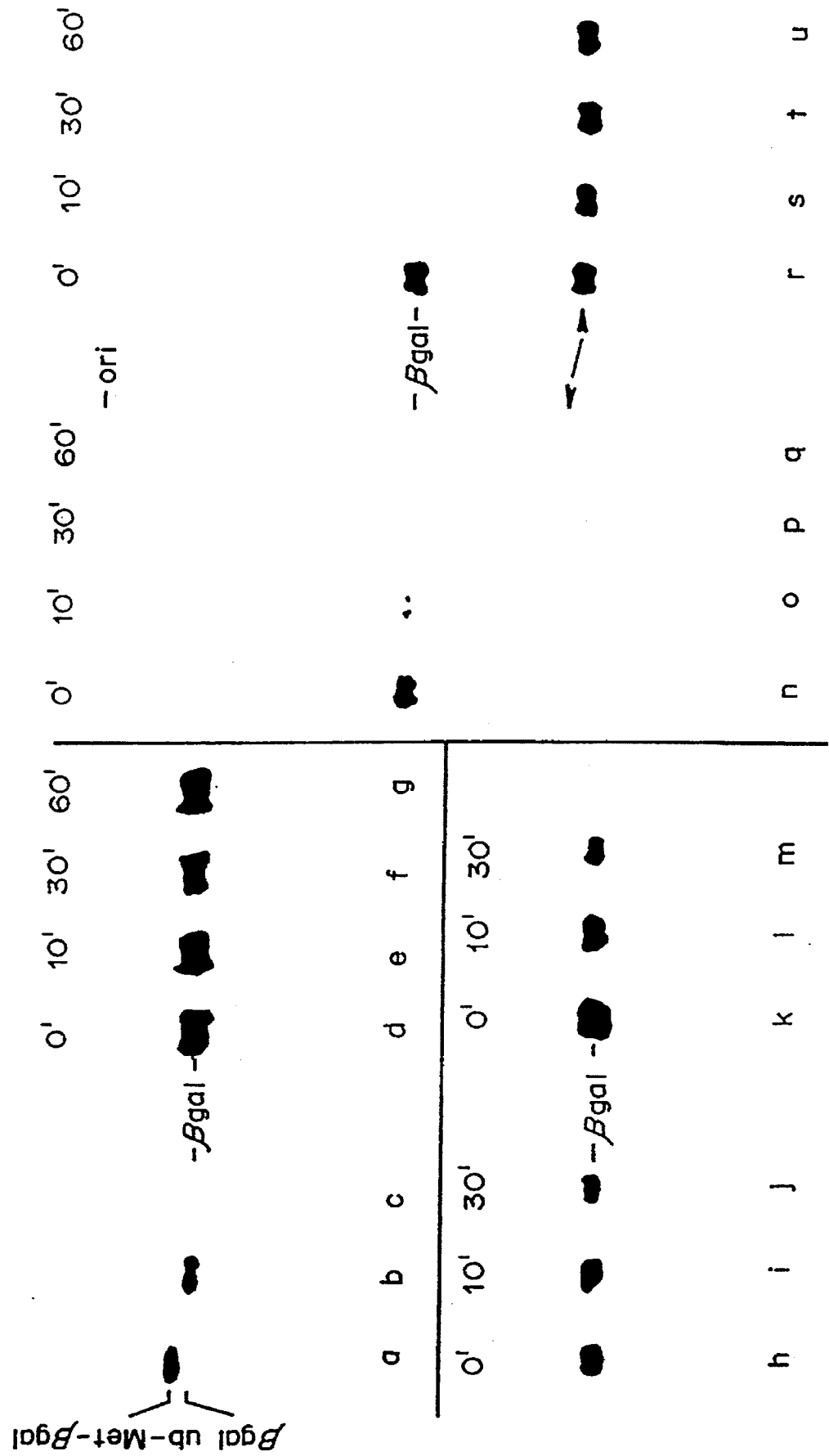
FIG. 2 shows experiments in which the half-lives of engineered β-gal proteins are directly measured.

FIG. 2 shows that the in vivo half-life of βgal is a function of its amino-terminal residue. (lane a) Minicells isolated from an *E. coli* strain carrying pUB23, the initial ub-lacZ fusion (FIGS. 1 and 3B), were labeled with [$^{35}$S]methionine for 60 minutes at 36° C., with subsequent analysis of βgal as described. The same result was obtained when the labeled minicell SDS extract was combined with an unlabeled yeast SDS extract before immunoprecipitation of βgal. (lane b) *S. cerevisiae* cells carrying pUB23 (FIG. 1), which encodes ub-Met-βgal (FIG. 3B), were labeled with [$^{35}$S]methionine for 5 minutes at 30° C., with subsequent analysis of βgal. The same result was obtained with the lengths of the [$^{35}$S]methionine labeling periods from 1 to 30 minutes, and with yeast extracts produced either by mechanical disruption of cells in the presence of protease inhibitors or by boiling the cells directly in an SDS-containing buffer. (lane c) Same as lane a but with *E. coli* cells carrying the control plasmid pLGSD5 (called G1 in L. Guarente, supra.) which encodes βgal. (lanes d to g) *S. cerevisiae* cells carrying pUB23 (FIG. 1), which encodes ub-Metβgal (FIG. 3A), were labeled with [$^{S}$]methionine for 5 minutes at 30° C. (lane d) followed by a chase in the presence of cycloheximide for 10, 30, and 60 minutes (lanes e to g), extraction, immunoprecipitation, and analysis of βgal. (lanes h to j) Same as lanes d to f, but with ub-Ile-βgal (see FIG. 3A). (lanes k to m) Same as lanes h to j, but with ub-Gln-βgal. (lanes n to q) Same as lanes d to g, but with ub-Leu-βgal. (lanes r to u) Same as lanes d to g, but with ub-Arg-βgal. Designations: ori; origin of the separating gel; ub, ubiquitin; βgal, an electrophoretic band of the βgal protein containing a specified amino-terminal residue; in this terminology, the Met-βgal portion of ub-Met-βgal is designated as βgal. Arrowheads denote a metabolically stable, about 90 kD degradation product of βgal which is formed apparently as the result of an in vivo endoproteolytic cleavage of a proportion of short-lived gal proteins such as Leu-βgal and Arg-βgal (lanes n to u).

FIG. 3 shows the changing amino acid residues of gal at the ubiquitin-βgal junction. (A) The initial plasmid, pUB23 (FIG. 1), which encodes ub-Met-βgal, was mutagenized as described above to convert the original Met codon ATG at the ub- gal junction into codons specifying 19 amino acids other than Met. (The original round of mutagenesis shown in FIG. 3, produced 15 out of 19 possible substitutions. The remaining four substitutions were produced later (see Table 1)). The arrowhead indicates the site of the deubiquitinating in vivo cleavage in the nascent fusion protein that occurs with all of the fusion proteins except ub-Pro-βgal (see text). All of the constructions shown encode His as the second gal residue. In addition, in some of the constructions (ub-Met-His-Gly-βgal, ub-Met-Gln-Gly-βgal, and ub-Met-Gln-His-Gly-βgal, the last one produced by an insertion mutation, see Table 3), either His or Gln were following Met at the ubiquitin-βgal junction, with indistinguishable consequences for the metabolic stabilities of the corresponding βgal proteins. (B) The amino acid sequence (in single-letter abbreviations) of ub-Met-βgal, the initial fusion protein (FIG. 1), in the vicinity of the ub-βgal junction. Single-letter amino acid abbreviations: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; Y, Tyr.

Figure 4:
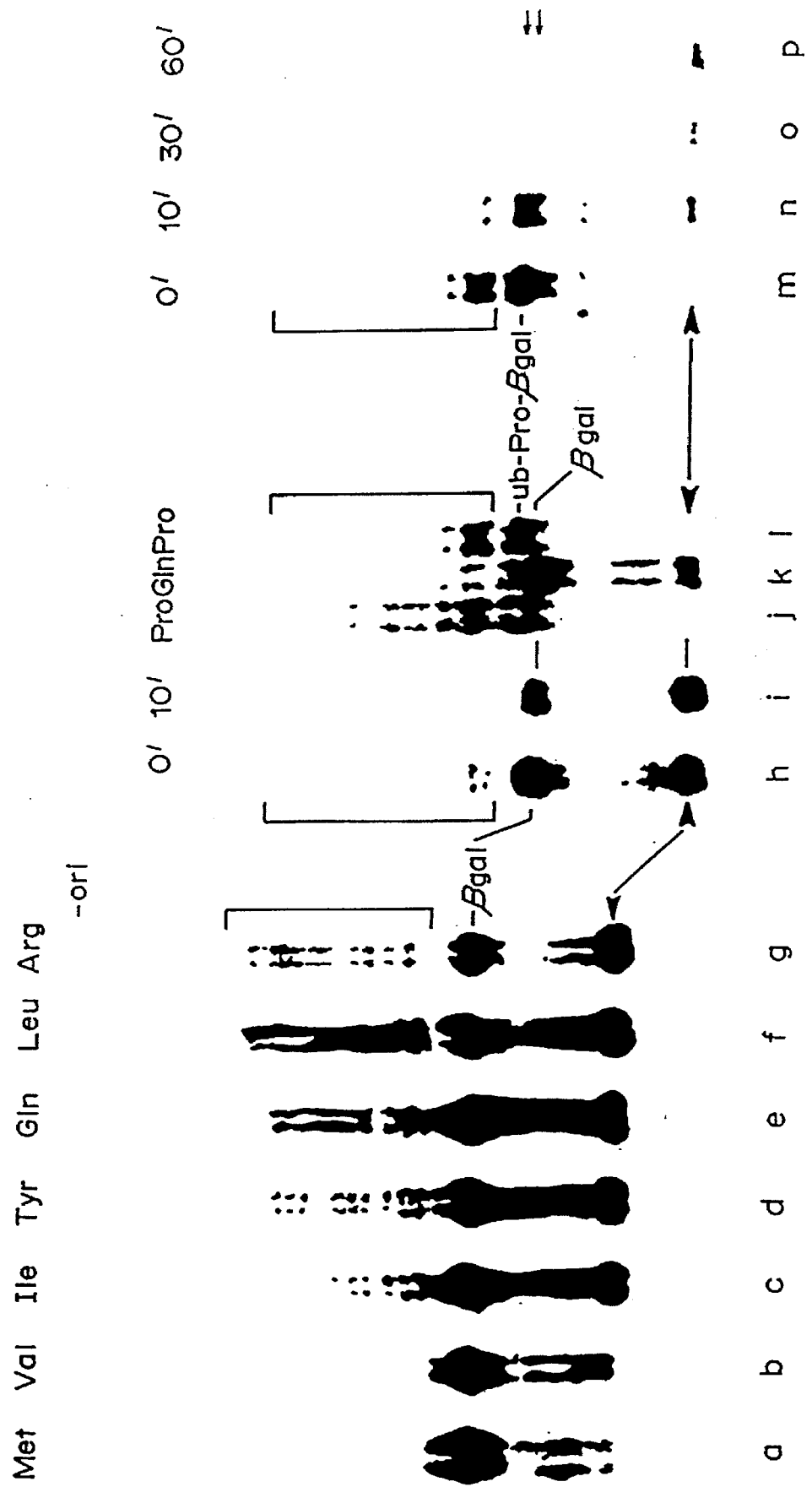
FIG. 4 shows the presence of multiple ubiquitin moieties in metabolically unstable β-gal proteins.

FIG. 4 shows that ubiquitin-βgal is short-lived if not deubiquitinated. (lanes a to g) S. cerevisiae cells carrying plasmids encoding ub-X-βgal fusion proteins in which X is the residue indicated at the top of each lane, were labeled for 5 minutes at 30° C. with [$^{35}$S]methionine, followed by extraction, immunoprecipitation and analysis of βgal. Fluorographic exposures for these lanes were several times longer than those for similar patterns in FIG. 2 to reveal the multiple ubiquitination of short-lived βgal proteins. (lanes h, i) Fluorographic overexposure of lanes n, o in FIG. 2 to reveal the "ladder" of multiply ubiquitinated Leu-βgal proteins in a pulse-chase experiment (zero and 10 minutes chase, respectively). (lane j) Same as lanes a to g, but with ub-Pro-βgal. (lane k) Same as lane j, but with ub-Gln-βgal. (lane l) Same as lane j. (lanes m to p) S. cerevisiae cells carrying a plasmid encoding ub-Pro-βgal were labeled for 5 minutes at 30° C. with [$^{35}$S]methionine (lane m) followed by a chase in the presence of cycloheximide for 10, 30, and 60 minutes (lanes n to p). The upper small arrow to the right of lane p denotes ub-Pro-βgal, a small proportion of which is still present after 1 hour chase. The lower small arrow indicates an apparently deubiquitinated Pro-βgal that slowly accumulates during chase and is metabolically stable. The dot to the left of lane m denotes an endogeneous yeast protein that is precipitated in some experiments by the antibody used. Square brackets denote the multiply ubiquitinated β-gal species (see FIG. 5). Other designation are as in FIG. 2.

Figure 5:
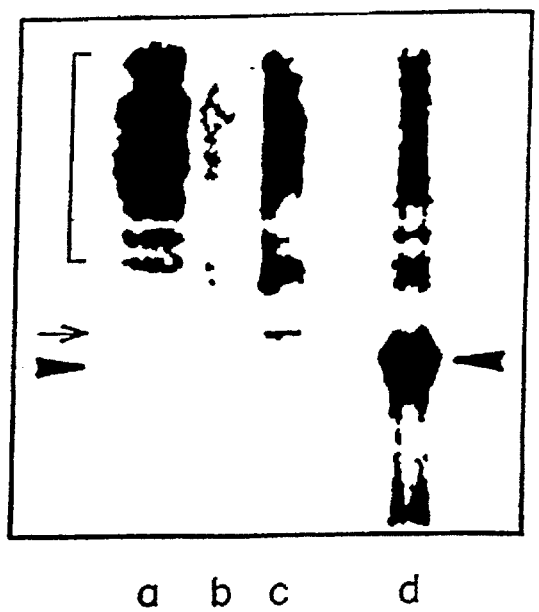
FIG. 5 shows a series of β-gal species containing ubiquitin in metabolically unstable β-gal proteins.
Figure 6A:
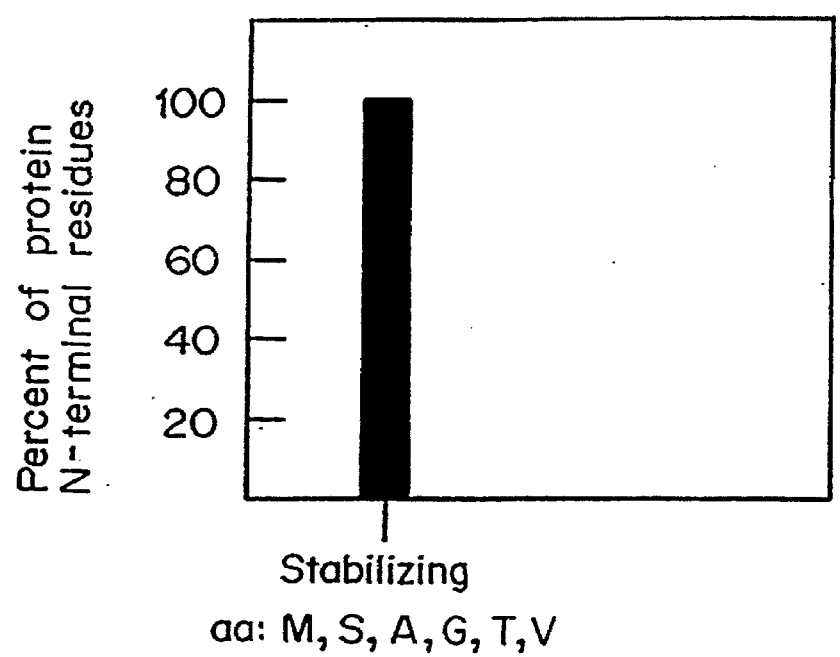
FIGS. 6A–6D show that both prokaryotic and eukaryotic long-lived intracellular proteins have stabilizing amino acid residues at their amino-termini whereas secreted proteins exhibit a complementary bias.
Figure 6B:
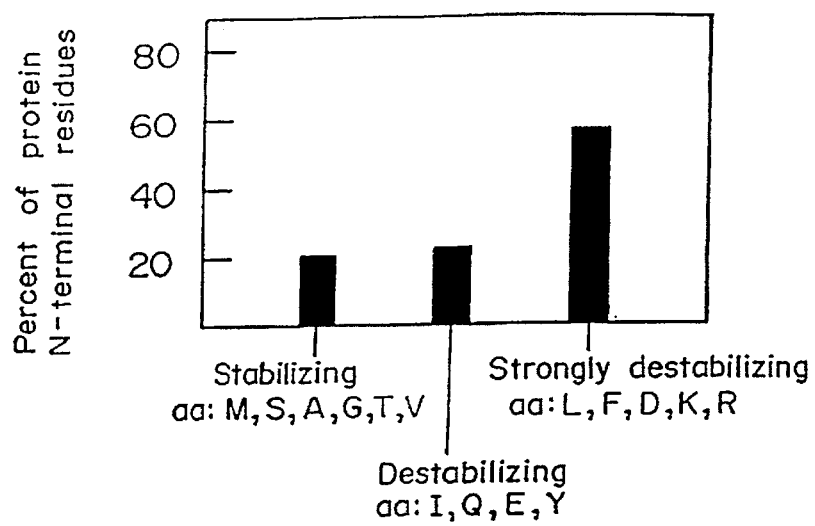
Figure 6C:
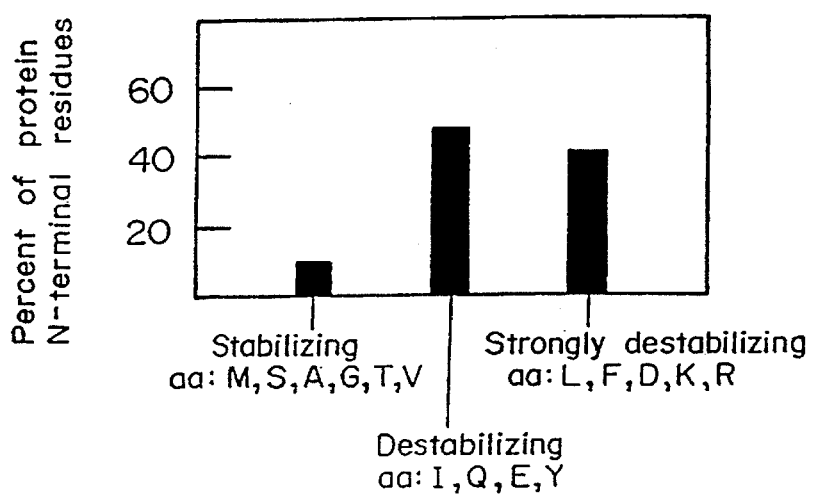
Figure 6D:
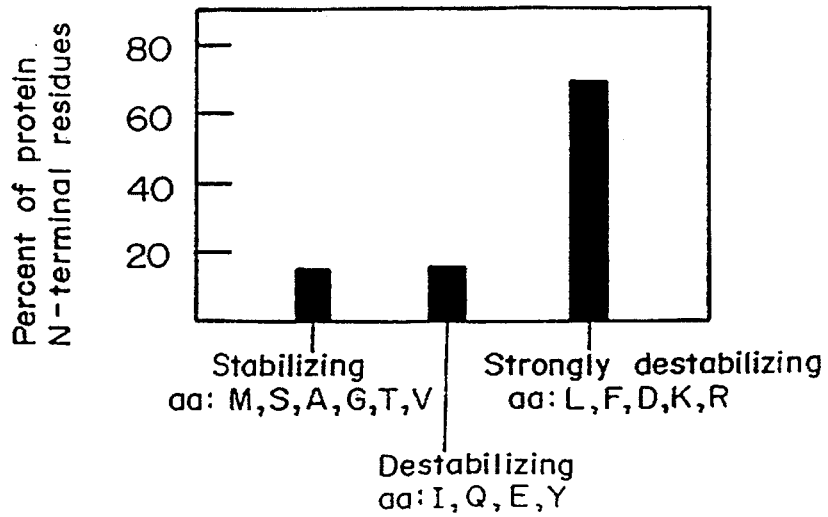

FIG. 5 shows the "ladder" βgal species containing ubiquitin. (lane a) S. cerevisiae cells carrying a plasmid which encodes ub-Gln-βgal, were grown and disrupted, and the extracts processed for isolation of βgal proteins by affinity chromatography on a column with immobilized antibody to βgal. The βgal proteins thus obtained were electrophoresed in a polyacrylamide-SDS gel, transferred to nitro-cellulose, and probed with an antibody to ubiquitin. (lane b) Same as lane a, but with ub-Pro-βgal. (lane c) Same as b but a longer autoradiographic exposure. (lane d) S. cerevisiae cells carrying a plasmid which encodes ub-Leu-βgal were labeled with [$^{35}$S]methionine for 5 minutes, with subsequent extraction, immunoprecipitation and electrophoresis of βgal (the same sample as in FIG. 4, lane f). Square brackets denote the multiply ubiquitinated Gln-βgal species detected with antibody to ubiquitin. The arrow indicates the band of ub-Pro-βgal, the initial fusion protein seen in lanes b and c. The arrowheads indicate the position of the band of deubiquitinated βgal (detectable by either Coomassie staining or metabolic labeling, but not with antibody to ubiquitin) derived from the ub-Gln-βgal fusion protein.

FIG. 6 shows both prokaryotic and eukaryotic long-lived intracellular proteins have stabilizing amino acid residues at their amino-termini, whereas secreted proteins exhibit a complementary bias.

(A) 208 long-lived, directly sequenced, intracellular (noncompartmentalized) proteins with unblocked amino-termini from both prokaryotes (77 proteins) and eukaryotes (131 proteins) were distributed into three groups according to the nature of their amino-terminal residues as defined by the N-end rule (Table 1). All of the long-lived intracellular proteins examined bear exclusively stabilizing residues at their amino-termini. In panels B to D, analogous diagrams are presented for 243 secreted eukaryotic proteins (B), for 37 light and heavy immunoglobulin chains (C), and for 94 secreted eukaryotic toxins (D). Entries in C and D are subsets of entries in B. For proteins in B to D, the amino-termini compiled correspond, whenever the assignment is possible, to the most processed form of a protein that is still located within a secreting cell. The data in A to D were manually compiled from the entire set of complete protein sequences available before 1981. The same conclusions have been recently reached after a more detailed and extensive, computer-assisted tabulation of protein amino-termini using the current National Biomedical Research Foundation database. The amino-terminal residues of Asn, Cys, His, and Trp were excluded from the compilation because in vivo half-lives of the corresponding βgal proteins are still unknown (see, however, the legend to Table 1). Inclusion of the residues (Table 1) into a recently compilation of the same type did not change the original conclusion. Although the amino-terminal Pro was also excluded from the compilation, Pro appears to be a stabilizing residue for βgal (Table 1), consistent with the frequent presence of Pro at the amino-termini of long-lived noncompartmentalized proteins.

FIG. 7 shows the construction of ubiquitin fusions with mouse dihydrofolate reductase.

FIG. 8 shows a greater range of specific dihydrofolate reductase (DHFR)-based protein constructs which have in common the DHFR moiety, and differ exclusively in the specific amino-terminal extensions attached to DHFR. Structure I is an initial DHFR construct. Structure II contains the 40-residue amino-terminal extension derived from the amino-terminus of βgal (see FIG. 3). Structures III–V are variants of Structure II in which either one or both of the lysine residues (denoted as K in the single-letter code, see the legend to FIG. 3) were replaced by the arginine residues (denoted as R). Structures V–X are variants of the Structure II with increasing deletions in the carboxyl-terminal half of the βgal-derived extension. Structures XI–XIII are variants of Structure II with increasing deletions in the amino-terminal half of the βgal-derived extension. Single-letter amino acid designations of the amino-termini of Structure I–XIII indicate variants of these protein constructs that differ exclusively in their amino-terminal residues. These variants were obtained through the use of the ubiquitin-protein fusion approach described herein (see FIG. 3). Each of the Structures I–XIII was constructed at the DNA level using site-directed mutagenesis and other methods of recombinant DNA technology currently standard in the field. These DNA constructs were introduced into the yeast *S. cerevisiae*, and the half-lives (left column of FIG. 8) of the corresponding proteins I–XIII were directly determined using the methods described above for βgal and a monospecific antibody to DHFR.

Results and Discussion

Rapid in vivo deubiquitination of a nascent ubiquitin-βgal fusion protein

Branched ubiquitin conjugates in which the carboxyl-terminal glycine of ubiquitin moieties is joined via an isopeptide bond to the α-amino groups of internal lysine residues in proteins apparently comprise the bulk of ubiquitin conjugates in eukaryotic cells. Joining of ubiquitin to the amino-terminal α-amino groups of target proteins, to yield linear ubiquitin conjugates, may also be chemically feasible. See A. Hershko, et al., *PNAS USA* 81: 7021 (1984). Whether or not linear ubiquitin-protein fusions are actually synthesized in vivo through posttranslational enzymatic conjugation of ubiquitin to protein amino-termini, such proteins can also be produced by constructing appropriate chimeric genes and expressing them in vivo. Construction of one such gene, which encodes yeast ubiquitin linked to βgal of *Escherichia coli*, is shown in FIG. 1.

When this gene is expressed in *E. coli*, the resulting βgal-containing protein has an apparent molecular mass which is approximately 6 kD greater that that of the control βgal, a value consistent with the presence of ubiquitin in the protein encoded by the chimeric gene. In contrast, when the same gene is expressed in yeast, the corresponding βgal protein is electrophoretically indistinguishable from the control βgal. This result is independent of the length of the [$^{35}$S]methionine labeling period (between 1 and 30 minutes). Furthermore, determination of the amino-terminal residue in the putative Met-βgal (half-life, $t_{1/2}$20 hours) by Edman degradation of the in vivo-labeled, gel-purified βgal (FIG. 2, lane d) directly confirmed the presence of the expected Met residue (FIG. 3A and Table 1) at its amino-terminus. Independent evidence that ubiquitin cleavage of the fusion protein occurs immediately after the last Gly residue of ubiquitin is presented below. We conclude that in yeast, ubiquitin is efficiently cleaved off the nascent ubiquitin-βgal fusion protein, yielding a deubiquitinated βgal. The absence of the deubiquitination reaction in *E. coli* is consistent with other lines of evidence indicating that prokaryotes lack both the eukaryotic ubiquitin and ubiquitin-specific enzymes. At the same time, the possibility remains that a functional counterpart of ubiquitin exists in bacteria but is different in its amino acid sequence from that of eukaryotic ubiquitin. The present invention clearly applies not only to the extremely close amino acid homologs of ubiquitin such as those found in eukaryotes but also to functional homologs of ubiquitin such as those that may exist in bacteria.

The ubiquitin-βgal junction encoded by the chimeric gene, Gly-Met (FIGS. 1 and 3B), is identical to the junctions between adjacent repeats in the polyubiquitin precursor protein, which is efficiently processed into mature ubiquitin. Thus it is likely that the same protease, as yet uncharacterized biochemically, is responsible both for the conversion of polyubiquitin into mature ubiquitin and for the deubiquitination of the nascent ubiquitin-βgal protein. If so, one potential way to inhibit the in vivo deubiquitination of the ubiquitin-βgal (and thereby to allow analysis of metabolic consequences of a stable ubiquitin attachment to βgal) would be to convert the Met residue of βgal at the ubiquitin-βgal junction (FIG. 3B) into other amino acid residues (FIG. 3A). The unexpected results of such an approach are described below.

The in vivo half-life of βgal is a function of its amino-terminal residue.

The ATG codon which specifies the original Met residue of gal at the ubiquitin junction (FIG. 3B) was converted by site-directed mutagenesis into codons specifying 19 other amino acids (See FIG. 3A and Table 1). These constructions differ exclusively in the first codon of βgal at the ubiquitin-βgal junction (FIG. 3A). After each of the 16 plasmids thus designed was introduced into yeast, analysis of the corresponding βgal proteins pulse-labeled in vivo led to the following results (FIGS. 2, 4, and Table 1):

1) With one exception (see below), the efficient deubiquitination of the nascent ubiquitin- gal occurs irrespective of the nature of the amino acid residue of βgal at the ubiquitin-βgal junction. Thus, the apparently ubiquitin-specific protease that cleaves the original ubiquitin-βgal protein at the Gly-Met junction is generally insensitive to the nature of the first residue of βgal at the junction (FIG. 3A and Table 1). This result, in effect, makes it possible to expose different amino acid residues at the amino-termini of the otherwise identical βgal proteins produced in vivo.

2) The in vivo half-lives of the βgal proteins thus designed vary from more than 20 hours to less than 3 minutes, depending on the nature of the amino acid residue exposed at the amino-terminus of βgal (FIGS. 2, 4, and Table 1). Specifically, deubiquitinated βgal proteins with either Met, Ser, Ala, Thr, Val, Cys or Gly at the amino-terminus have relatively long in vivo half-lives of 20 hours or more (FIG. 2, lanes d to g, and Table 1), similar to the half-life of a control βgal whose gene had not been fused to that of ubiquitin. In striking contrast, the βgal proteins with either Arg, Lys, Phe, Leu, Asp or Trp at the amino-terminus have very short half-lives, between approximately 2 minutes for Arg-βgal and approximately 3 minutes for Lys-βgal, Phe-βgal, Leu-βgal, Asp-βgal, Asn-βgal and Trp-βgal (FIG. 2, lanes n to u, and Table 1). The half-life of βgal proteins with amino-terminal residues of either Gln, His or Tyr is approximately 10 minutes (FIG. 2, lanes k to m, and Table 1), while an amino-terminal Ile or Glu confers on βgal a half-life of approximately 30 minutes (FIG. 2, lanes h to j, and Table 1). Both pulse-chase and continuous labeling techniques were used in these experiments and yielded similar results.

The set of individual amino acids can be ordered with respect to the half-lives that they confer on βgal when exposed at its amino-terminus. The resulting rule (Table 1) is referred to as the "N-end rule".

TABLE 1

The N-end rule

| Residue X in ub—X—βgal | Radius of gyration of X(A) | In vivo deubiquitination of nascent ub—X—βgal | $t_{1/2}$ of X—βgal |
|---|---|---|---|
| Met | 1.80 | + | |
| Ser | 1.08 | + | |
| Ala | 6.77 | + | |
| Thr | 1.24 | + | >20 hours |
| Val | 1.29 | + | |
| Gly | 0 | + | |
| Cys | | + | |

TABLE 1-continued

The N-end rule

| Residue X in ub—X—βgal | Radius of gyration of X(A) | In vivo deubiquitination of nascent ub—X—βgal | $t_{1/2}$ of X—βgal |
|---|---|---|---|
| Ile | 1.56 | + | |
| Glu | 1.77 | + | ~30 minutes |
| Tyr | 2.13 | + | |
| Gln | 1.75 | + | ~10 minutes |
| His | | | |
| Phe | 1.90 | + | |
| Leu | 1.54 | + | ~3 minutes |
| Trp | | + | |
| Asp | 1.43 | + | |
| Asn | | + | |
| Lys | 2.08 | + | |
| Arg | 2.38 | + | ~2 minutes |
| Pro | 1.25 | —* | ~7 minutes |

*The rate of in vivo deubiquitination of ub—Pro—βgal is extremely low. The $t_{1/2}$ shown is that of the initial ub—Pro—βgal fusion protein (see FIG. 4, lanes j to p).
Legend to Table 1
The N-end rule. In vivo half-lives of βgal proteins in the yeast S. cerevisiae were determined either by the pulse-chase technique (for short-lived βgal's; see below) or by measuring the enzymatic activity of βgal in crude extracts. For the measurements of βgal activity, cells growing in a galactose-containing medium were transferred to an otherwise identical medium lacking galactose and containing 10 percent glucose. After further growth for at least 5 hours at 30° C., the ratio of βgal activities per cell before and after shift to glucose was determined for each of the βgal proteins. [GAL promoter-driven expression of the fusion genes (FIGS. 1 and 3) is repressed in glucose medium]. For shorter-lived βgal proteins ($t_{1/2}$ 1 hour), the pulse-chase technique was used as well (FIGS. 2 and 4). Electrophoretic bands of βgal proteins labeled with [$^{35}$S]methionine in pulse-chase experiments were cut out from scintillant-impregnated dried gels similar to those of FIGS. 2 and 4, and $^{35}$S in the bands was determined. The in vivo decay of short-lived βgal proteins deviated from first-order kinetics in that the rate of degradation was lower when measured at later (1 hour) time points of the chase, the lower rate reflecting either a time-dependent toxic effect of cycloheximide or intrinsic characteristics of the in vivo degradation process. [Arrest of translationis required for an efficient short-term chase in S. cerevisiae because of the amino acid pool equilibration problems related to the presence of vacuoles in this organism]. The half-life values listed below were determined for the first 10 minutes of chase. Several lines of evidence (see description of FIGS. 4 and 6) suggest that Pro is a stabilizing residue. The listed radii of gyration of amino acids are from. M. Levitt, J. Mol. Biol. 104:59 (1976).

Deubiquitination of Ub-X-βgal fusion proteins in ATP-depleted reticulocyte extract.

Each of twenty $^{35}$S-labelled Ub-X-βgal proteins prepared in E. coli as described above, was added to an extract prepared from ATP-depleted rabbit reticulocytes (Etlinger et al., Proc. Natl. Acad. Sci. USA 74: 54 (1977); Hershko et al., Proc. Natl. Acad. Sci. USA 77: 1783 (1980); Hershko et al., J. Biol. Chem. 258: 8206 (1982)), and the fates of the added proteins were followed by SDS-polyacrylamide gel electrophoresis (SDS-PAGE). As had been observed in vivo with the same ubiquitin fusions in yeast, an apparently ubiquitin-specific protease in reticulocyte extract deubiquitinated the added Ub-X-βgal fusion proteins to yield the corresponding X-βgal test proteins. The deubiquitination of 19 out of the 20 Ub-X-βgal proteins in the ATP-depleted extract was more than 90% complete in 5 minutes at 37° C. (Table 2). The single exception, both in yeast and in reticulocytes, is Ub-Pro-βgal, which was deubiquitinated approximately 20 times more slowly than were the other Ub-X-βgal proteins.

Amino acid sequencing (by Edman degradation) of deubiquitinated βgal proteins reisolated from either the reticulocyte extract or yeast cells showed that, in every case tested, the proteolytic cleavage occured precisely at the Ub-βgal junction (Table 2). Although sequencing revealed that the amino termini of some X-βgal proteins underwent specific modificiations (see Table 2), in no case did these modifications involve proteolytic cleavages beyond the amino-terminal residue X.

All of the deubiquitinated X-βgal proteins were metabolically stable in the ATP-depleted reticulocyte extract as judged from SDS-PAGE analysis and from the negligible production of acid-soluble radioactivity in the extract. Thus, preincubation of Ub-X-βgal fusion proteins in the ATP-depleted reticulocyte extract makes it possible to generate twenty X-βgal test proteins which differ exclusively at the amino-terminal residue X.

Half-life of a βgal protein in ATP-supplemented reticulocyte extract is a function of βgal's amino-terminal residue.

While all of the twenty X-βgal proteins were metabolically stable in the ATP-depleted reticulocyte extract, most of them became short-lived upon addition of ATP to the extract (Table 2). We refer to an amino-terminal residue as stabilizing if the corresponding X-βgal is relatively long-lived in the ATP-supplemented extract (less than 10% degradation in 2 hours at 37° C.), and as destabilizing if the degradation of the corresponding X-βgal in the extract exceeds 15% under the same conditions (Table 2).

The time courses of degradation for several X-βgal proteins showed reproducible initial lags. However, semilogarithmic plots of the time courses showed that, after the initial lags, the degradation of X-βgal in the ATP-supplemented reticulocyte extract obeyed first-order kinetics for at least the first two hours, making it possible to compare the degradation of different X-βgal proteins by comparing their half-lives in the extract (Table 2).

The range of βgal half-lives in the reticulocyte extract encompasses more than two orders of magnitude, from approximately 50 minutes for Gln-βgal to approximately 100 hours for Val-βgal (Table 2). The half-lives of X-βgal proteins bearing stabilizing amino-terminal residues range from approximately 20 hours for Ile-βgal to approximately 100 hours for Val-βgal. Half-lives of the metabolically unstable X-βgal proteins in the reticulocye extract were comparable to the half-lives of other proteolytic substrates (iodinated serum albumin, lysozyme, and cytochrome c) in the same extract. These latter test proteins have been used in earlier studies of ubiquitin-dependent protein degradation in reticulocye extract (Finley et al., Trends Biochem. Sci. 10: 343 (1985); Etlinger et al., Proc. Natl. Acad. Sci. USA 74: 54 (1977)). Recently, at least some of these proteins have been shown to be targeted for degradation via their destabilizing amino-terminal residues [Reiss et al., J. Biol. Chem. 263: 2693 (1988)] as defined by the N-end rule.

TABLE 2

The N-end rule in yeast and in mammalian reticulocytes.

| | Half-life of X—βgal | | Amino terminus of reisolated X—βgal | |
|---|---|---|---|---|
| | Yeast | Mammalian | as determined by protein sequencing | |
| Residue X in Ub—X—βgal | (S. cerevisiae) in vivo | reticulocytes in vitro | Yeast in vivo | Reticulocytes in vitro |
| Val | >20 hours | 100 hours | — | Val—βgal$^{d,e}$ |
| Met | >20 hours | 30 hours | Met—βgal$^a$ | Met—βgal$^{d,e}$ |
| Gly | >20 hours | 30 hours | — | Gly—βgal$^{d,e}$ |
| Pro | >20 hours$^j$ | >20 hours$^j$ | —$^i$ | —$^i$ |
| Ala | >20 hours | 4.4 hours | Ala—βgal$^b$ | Ala—βgal$^{d,f}$ |
| Ser | >20 hours | 1.9 hours | —$^h$ | Ser—βgal$^{d,f}$ |
| Thr | >20 hours | 7.2 hours | Thr—βgal$^b$ | Thr—βgal$^{d,f}$ |
| Cys | >20 hours | 1.2 hours | — | [?]-βgal$^g$ |
| Ile | 30 minutes | 20 hours | Ile—βgal$^{b,c}$ | Ile—βgal$^{d,e}$ |
| Glu | 30 minutes | 1.0 hours | Arg—Glu—βgal$^c$ | Glu—βgal + Arg—Glu—βgal$^d$ / Arg—Glu—βgal$_f$ |
| His | 10 minutes | 3.5 hours | — | His—βgal$^d$ |
| Tyr | 10 minutes | 2.8 hours | Tyr—βgal$^{b,c}$ | Tyr—βgal$^d$ |
| Gln | 10 minutes | 0.8 hours | [?]-Glu—βgal$^j$ | [?]-Glu—βgal + Glu—βgal$^{d,k}$ / Arg—Glu—βgal$_f$ |
| Asp | 3 minutes | 1.1 hours | Arg—Asp—βgal$^c$ | Asp—βgal + Arg—Asp—βgal$^d$ / Arg—Asp—βgal$_f$ |
| Asn | 3 minutes | 1.4 hours | Arg—Asp—βgal$^c$ | Asn—βgal + Asp—βgal$^d$ / Asn—βgal + Arg—Asp—βgal$_f$ |
| Phe | 3 minutes | 1.1 hours | — | Phe—βgal$^d$ |
| Leu | 3 minutes | 5.5 hours | — | Leu—βgal$^d$ |
| Trp | 3 minutes | 2.8 hours | — | Trp—βgal$^d$ |
| Lys | 3 minutes | 1.3 hours | — | Lys—βgal$^d$ |
| Arg | 2 minutes | 1.0 hours | — | Arg—βgal$^d$ |

Amino-terminal location of an amino acid is essential for its effect on βgal half-life as tested in yeast Site-directed mutagenesis was employed to insert a codon specifying a "stabilizing" amino acid (in this experiment, the Met residue) before the first codon of βgal at the ubiquitin-βgal junction (Table 3). Insertion of a stabilizing residue (Met) before either another stabilizing residue (Thr) or a variety of destabilizing residues (Gln, Lys, and Arg) at the ubiquitin-βgal junction invariably results in a long-lived deubiquitinated βgal (Table 3). Furthermore, in contrast to ubiquitin-Pro-βgal which is not only short-lived but also resistant to deubiquitination (FIG. 4, lanes j to p, and Table 1), ubiquitin-Met-Pro-βgal is efficiently deubiquitinated in vivo to yield a long-lived Met-Pro-βgal (Table 3). These results show that both the identity of amino acid residue and its amino-terminal location (presumably the presence of a free α-amino group) are essential for its effect on βgal half-life. In addition, these results (Table 3) further support the expectation that ubiquitin-specific cleavage of the fusion protein occurs immediately after the last Gly residue of ubiquitin (FIG. 3A).

TABLE 3

| Fusion protein | N-terminal location of an amino acid is essential for its effect on βgal half-life $t_{1/2}$ of deubiquitinated fusion protein |
|---|---|
| ub—Thr—βgal | >20 hours |
| ub—Met—Thr—βgal | >20 hours |
| ub—Gln—βgal | ≈10 minutes |
| ub—Met—Gln—βgal | >20 hours |
| ub—Lys—βgal | ≈3 minutes |
| ub—Met—Lys—βgal | >20 hours |
| ub—Arg—βgal | ≈2 minutes |
| ub—Met—Arg—βgal | >20 hours |
| ub—Pro—βgal | ≈7 minutes* |

TABLE 3-continued

N-terminal location of an amino acid is
essential for its effect on βgal half-life

| Fusion protein | $t_{1/2}$ of deubiquitinated fusion protein |
|---|---|
| ub—↓—Met—Pro—βgal | >20 hours |

Amino-terminal location of an amino acid is essential for its effect on βgal half-life. The insertion mutants were obtained essentially as described for the initial set of mutants except that a 32-residue oligonucleotide, 5'-CCCGGGATCCGTGC(G/C/T/) (G/T) CATACCACCTCTTAG was used, containing 14 bases on the 5' side and 15 bases on the 3' side of the ambiguous codon inserted behind the Met codon. Bases in parentheses denote ambiguities at the positions 16 and 17 in the sequence. Half-lives of the corresponding βgal proteins were determined as described in the legend to Table 1.

A long-lived cleavage product of βgal is formed during decay of short-lived βgal proteins.

The electrophoretic patterns of short-lived (but not of long-lived) βgal proteins invariably contain a specific, about 90 kD cleavage product of βgal (FIG. 2, lanes n to u) which, unlike the parental βgal species, accumulates during the postlabeling (chase) period (FIG. 4, lanes m–p). The 90 KD βgal fragment constitutes a relatively small proportion of the initial amount of the pulse-labeled βgal. Nonetheless, its existence implies that an in vivo endoproteolytic cleavage can rescue a protein fragment from the metabolic fate of its short-lived parental protein. It remains to be seen whether the resulting possibility of multiple half-lives within a single protein species is exploited in the design of naturally short-lived proteins.

Ubiquitin-βgal is short-lived when not deubiquitinated.

Ubiquitin-Pro-βgal, the only ubiquitin-βgal fusion that is not deubiquitinated in vivo (FIG. 4, lanes j to p), has a half-life of approximately 7 minutes (Table 1) which is less than 1 percent of the half-life of metabolically stable βgal proteins (Table 1). One interpretation of this result is that a metabolically stable ubiquitin attachment to protein amino-termini is sufficient to signal degradation of acceptor proteins. This interpretation is consistent with earlier biochemical and genetic evidence that ubiquitination of short-lived proteins in a mammalian cell is essential for their degradation. At the same time, all ubiquitin-βgal fusion proteins other than ubiquitin-Pro-βgal are rapidly deubiquitinated in vivo (Table 1). Thus, the posttranslational amino-termal ubiquitination of proteins may not be involved in an initial recognition or commitment step that designates proteins for degradation in vivo. Whether posttranslational amino-terminal ubiquitination (if it actually occurs in vivo) is essential for later stages of the degradation pathway remains to be determined. Earlier in vitro experiments indicated that preferential chemical modification of amino-termini of proteolytic substrates inhibits their degradation in an in vitro ubiquitin-dependent proteolytic system. Based on these data, it was proposed that amino-terminal ubiquitination of proteins is essential for their degradation. An alternative interpretation of the same results is that chemical blocking of proteins' amino-termini prevents the recognition of their amino-terminal residues by the "N-end rule" pathway whose initial stages are not necessarily ubiquitin-dependent.

Short-lived βgal proteins are multiply ubiquitinated in vivo.

Overexposures of the pulse-chase fluorograms (FIG. 2) reveal that the major band of a deubiquitinated, short-lived βgal protein coexists with a "ladder" of larger molecular mass, βgal-containing bands irregularly spaced at 4 to 7 kD intervals (FIG. 4, lanes c to g). No such larger species appear when the fluorograms of long-lived βgal proteins are similarly overexposed (FIG. 4, lanes a and b). Immunological analysis with both antibodies to βgal and antibodies to ubiquitin demonstrates that the "ladder" βgal species contain ubiquitin (FIG. 5).

A model for the selective degradation pathway. With the exception of natural or engineered ubiquitin fusion proteins (FIG. 1 and Table 1), nascent proteins apparently lack ubiquitin moieties. The in vivo amino-terminal processing of nascent noncompartmentalized proteins generates their mature amino-termini via the action of amino-terminal peptidases whose substrate specificities have been partially characterized. (See Tsunasawa, S. et al. *J. Biol. Chem.* 260 5382 (1985); Boissel, J. P. et al. *PNAS USA* 82, 8448 (1985)). We suggest that the amino-termini thus generated are recognized by an "N-end-reading" enzyme. One specific model is that a commitment to degrade a protein molecule is made as a result of the recognition of its amino-terminal residue by a stochastically operating enzyme whose probability of "clamping" at the target's amino-terminus is determined by the N-end rule (Table 1). Once the commitment is made, it is followed by a highly processive ubiquitination of the target protein which in the case of βgal is conjugated to more than 15 ubiquitin moieties per molecule of βgal (FIG. 4, lanes c to g, and FIG. 5). The multiply ubiquitinated target protein is then degraded by a "down stream" enzyme (1) for which the ubiquitin moieties of the target serve as either recognition signals or denaturation (unfolding) devices, or both.

The ubiquitin-containing "ladder" βgal species (FIG. 4, lanes c to 1, and FIG. 5) consist of apparently branched ubiquitin moieties joined to the α-amino groups of internal lysine residues in βgal. Surprisingly, the "ladder" βgal species derived from ubiquitin-Pro-βgal are electrophoretically indistinguishable from the analogous species of βgal whose amino-terminal ubiquitin is cleaved off the nascent fusion protein (FIG. 4, lanes j to 1, and FIG. 5). If the electrophoretically indistinguishable ubiquitinated βgal species are indeed structurally homologous, these results would be compatible with two alternative models in which, immediately after the first ubiquitins are branch-conjugated to βgal, either a branch-ubiquitinated ubiquitin-Pro-βgal undergoes amino-terminal deubiquitination or, alternatively, an analogous βgal species lacking the amino-terminal ubiquitin moiety reacquires it. Experimental resolution of this ambiguity may establish whether the posttranslational amino-terminal ubiquitination of proteins (if it occurs in vivo) plays a role in selective protein turnover.

Although both prokaryotic and eukaryotic proteins appear to follow the N-end rule (see below), bacteria apparently lack the ubiquitin system. Thus it is possible that the hypothetical N-end-recognizing protein is more strongly conserved Between prokaryotes and eukaryotes than is the rest of the selective degradation pathway. Interestingly, the properties of a mammalian protein E3 whose presence is required for ubiquitination of proteolytic substrates by ubiquitin-conjugating enzymes in vitro are consistent with it being a component of the N-end-recognizing protein.

The N-end rule and the known amino-termini of intracellular proteins.

The unblocked amino-terminal residues in metabolically stable, noncompartmentalized proteins from both prokaryotes and eukaryotes are exclusively (FIG. 6A) of the stabilizing class (Met, Ser, Ala, Gly, Thr, Val), that is, the class that confers long in vivo half-lives on βgal (Table 1). The one short-lived intracellular protein for which the mature amino-terminus is known is the cII protein of phage lambda, the central component of a trigger that determines whether lambda grows lytically or lysogenizes an infected cell. (Y. S. Ho, D. Wulff, M. Rosenberg, in *Regulation of Gene Expression*, I. Booth and C. Higgins, Eds. (Cambridge Univ. Press, London, 1986), p. 79; F. Banuett, M. A. Hoyt, McFarlane, H. Echols, I. Herskowitz, *J. Mol. Biol.* 187, 213 (1986); M. A. Hoyt, D. M. Knight, A. Das, H. I. Miller, H. Echols, *Cell* 31, 565 (1982); K. Nasmyth, Nature (london) 320, 670 (1983)). The half-life of cII in lambda-infected *E. coli* is less than 3 minutes. Strikingly, the mature amino-terminus of cII starts with Arg (Ho, Y. W. et al., *J. Biol. Chem.* 257, 9128 (1982)), the most destablizing residue in the N-end rule (Table 1).

While the destabilizing amino acids can be either hydrophobic, uncharged hydrophilic or charged, they share the property of having larger radii of gyration than any of the stabilizing amino acids except Met (Table 1).

Amino-terminal residues in compartmentalized proteins are largely of the destabilizing class.

FIG. 6 illustrates a striking difference between the choice of amino-terminal residues in long-lived, noncompartmentalized intracellular proteins (A) and in compartmentalized proteins, such as secreted proteins (B), many of which are also long-lived in their respective extracellular compartments. One implication of this finding is that a single intracellular degradation pathway operating according to the N-end rule could be responsible both for the diversity of in vivo half-lives of intracellular proteins and for the selective destruction of compartmentalized proteins that are aberrantly introduced into the intracellular space. Some miscompartmentalized proteins may be more harmful to the cell than others. It is therefore of interest that secreted eukaryotic toxins contain strongly destabilizing residues (Arg, Lys, Leu, Phe, Asp) at their amino-termini more often than the general population of secreted proteins (FIG. 6, panels B to D).

The above consideration also suggest that, if the topological outside of a cell, such as lumens of the endoplasmic reticulum and golgi, and the extracellular space, were to have degradation pathways analogous to the N-end rule pathway, they could be based on "inverted" versions of the N-end rule in which the amino-terminal residues that are destabilizing inside the cell are now the stabilizing ones and vice versa. Thus, the methods of the present invention should also be useful for manipulating the metabolic stability and other properties of compartmentalized proteins, including secreted ones.

Possible role of the N-end rule pathway in the turnover of long-lived proteins.

Long-lived intracellular proteins with destabilizing (Table 1) penultimate residues generally retain their initial amino-terminal methionine residue. The amino-terminal residues in long-lived intracellular proteins that do undergo amino-terminal processing are invariably of the stabilizing class (Table 1). An interesting possibility that would involve the N-end rule pathway in the turnover of long-lived proteins is that the rate-limiting step in the in vivo degradation of long-lived proteins may be a slow aminopeptidase cleavage that exposes a destabilizing residue, followed by rapid degradation via the N-end rule pathway. Note that fine-tuning of the rate of degradation may in this case be a function of the rate of aminopeptidase cleavage exposing a destabilizing residue rather than a function of the residue's destabilizing capacity according to the N-end rule.

The N-end rule and selective degradation of short-lived and damaged proteins.

The recognition of polypeptide chain folding patterns or of local chemical features that target an otherwise long-lived but damaged protein for selective degradation in vivo is unlikely to be mediated directly by the N-end rule pathway. Instead, we suggest that specific proteases (analogous in function to nucleases that recognize specific lesions in DNA) cleave a targeted protein so as to expose a destabilizing residue at the amino-terminus of one of the two products of a cut. One testable prediction of this model is that the initial cleavage products of the degradation pathway should bear destabilizing residues at their N-termini. The preferential exposure of destabilizing residues at the amino-termini of products of the initial protein cleavages may be due either to intrinsic specificities of the proteases involved or simply to the fact that a majority of the amino acids belong to the destabilizing class (Table 1). Furthermore, initial cleavages of a protein would be expected to destabilize aspects of its original conformation, thus increasing the probability of further internal cuts. Whether the initial cleavage products of a protein would be degraded exclusively via the N-end rule pathway or would have to be processed further by additional internal cleavages should depend on several factors, such as the exposure of destabilizing residues at the amino-termini of initial cleavage products, and the relative rates of introduction of internal cuts. In this model, the N-end rule pathway should be essential for degradation of most of the metabolically unstable proteins, from chemically damaged, prematurely terminated, improperly folded and miscompartmentalized ones to those that cannot assemble into native multisubunit aggregates, and finally to otherwise normal proteins that are short-lived in vivo. Thus, the metabolic instability of a protein may be mediated not only by the exposure of a destabilizing residue at its amino-terminus, but also by local conformational and chemical features of its polypeptide chain that result in proteolytic cleavages exposing destabilizing residues at the amino-termini of cleavage products.

For any given protein, a variety of factors in addition to the N-end rule may combine to modulate its half-life in vivo. Among such factors may be the flexibility and accessibility of the protein's amino-terminus (Thornton, J. M. and Sibanda, B. L., *J. Mol. Bio.* 167 443 (1983)), the presence of chemically blocking amino-terminal groups such as the acetyl group, the distribution of ubiquitinatable lysine residues near the amino-terminus, and other variables, such as the structure of the carboxy-terminus. Since amino-terminal regions of multisubunit proteins are commonly involved in the interfaces between subunits (Thornton, J. M. and Sibanda, B. L., *J. Mol. Bio.* 167 443 (1983)), quarternary structure of proteins is yet another parameter that is expected to modulate the impact of the N-end rule pathway on protein half-lives in vivo. Finally as suggested above, the N-end rule pathway may also be essential for the degradation of proteins whose initial recognition as targets for degradation is independent of the structures at their amino-termini.

Functional significance of posttranslational addition of amino acids to amino-termini of proteins.

It has been known for many years that in both bacteria and eukaryotes there exists an unusual class of enzymes, aminoacyl-transfer RNA-protein transferases, which catalyze posttranslational conjugation of specific amino acids to the mature amino-termini of acceptor proteins in vitro (R. L. Soffer, in *Transfer RNA:Biological Aspects*, D. Soll, J. N. Abelson, P. R. Schimmel, Eds. (Cold Spring Harbor Laboratory, Cold Spring Harbor, NY 1980), p493;C. Deutch, *Methods Enzymol.* 106, 198 (1984): A. Kaji, H. Kaji, G. D. Novelli, *J. Biol. Chem.* 240, 1185 (1965)). The posttranslational addition of amino acids to proteins in vivo dramatically accelerates in a stressed or regenerating tissue, for example, after physical injury to axons of nerve cells (S. Shyne-Athwal, R. V. Riccio, G. Chakraborty, N. A. Ingolia, *Science* 231, 603 (1986); N. A. Ingolia et al., *J. Neurosci* 3, 2463 (1983)). The N-end rule provides an explanation for this phenomenon. We suggest that selective changes in metabolic stability of otherwise undamaged, longlived proteins that may be required by a changed physiological state of the cell are brought about by posttranslational addition of destabilizing amino acids to the amino-termini of target proteins in vivo. Strikingly, the known reactions of posttranslational addition of amino acids to proteins (R. L. Soffer, in *Transfer RNA:Biological Aspects*, D. Soil, J. N. Abelson, P. R. Schimmel, Eds. (Cold Spring Harbor Laboratory, Cold Spring Harbor, NY 1980), p493; C. Deutch, *Methods Enzymol.* 106, 198 (1984); A. Kaji, H. Kaji, G. D. Novelli, *J. Biol. Chem.* 240, 1185 (1965); S. Shyne-Athwal, R. V. Riccio, G. Chakraborty, N. A. Ingolia, *Science* 231, 603 (1986); N. A. Ingolia et al., *J. Neurosci* 3, 2463 (1983)) involve largely those amino acids (Arg, Lys, Leu, Phe, and Tyr) that are destabilizing according to the N-end rule (Table 1). Physiological states in which addition of destabilizing amino acids to proteins could be expected to occur include entry to and exit from the cell cycle, responses to chemical or physical stress, and specific differentiation events, such as erythroid differentiation and spermatogenesis, in which a proportion of preexisting, otherwise longlived intracellular proteins is selectively degraded.

The in vitro degradation of some proteolytic substrates in a ubiquitin-dependent system from mammalian reticulocytes has recently been shown to depend on the presence of certain aminoacyl-tRNAs (Ferber, S. and Ciechanover, A., *J. Biol. Chem.* 261 3128 (1986)). We suggest that this phenomenon also reflects a requirement for posttranslational addition of specific destabilizing amino acids to the amino-termini of proteolytic substrates. The initial proteolytic substrates in question have amino-terminal residues of Asp or Glu, both of which are destabilizing according to the N-end rule (Table 1). This raises an interesting and testable possibility that certain amino-terminal residues in proteins may not be directly destabilizing as such but only through their ability to be conjugated to other destabilizing residues.

Ubiquitin fusions with dihydrofolate reductase

Figure 7A:
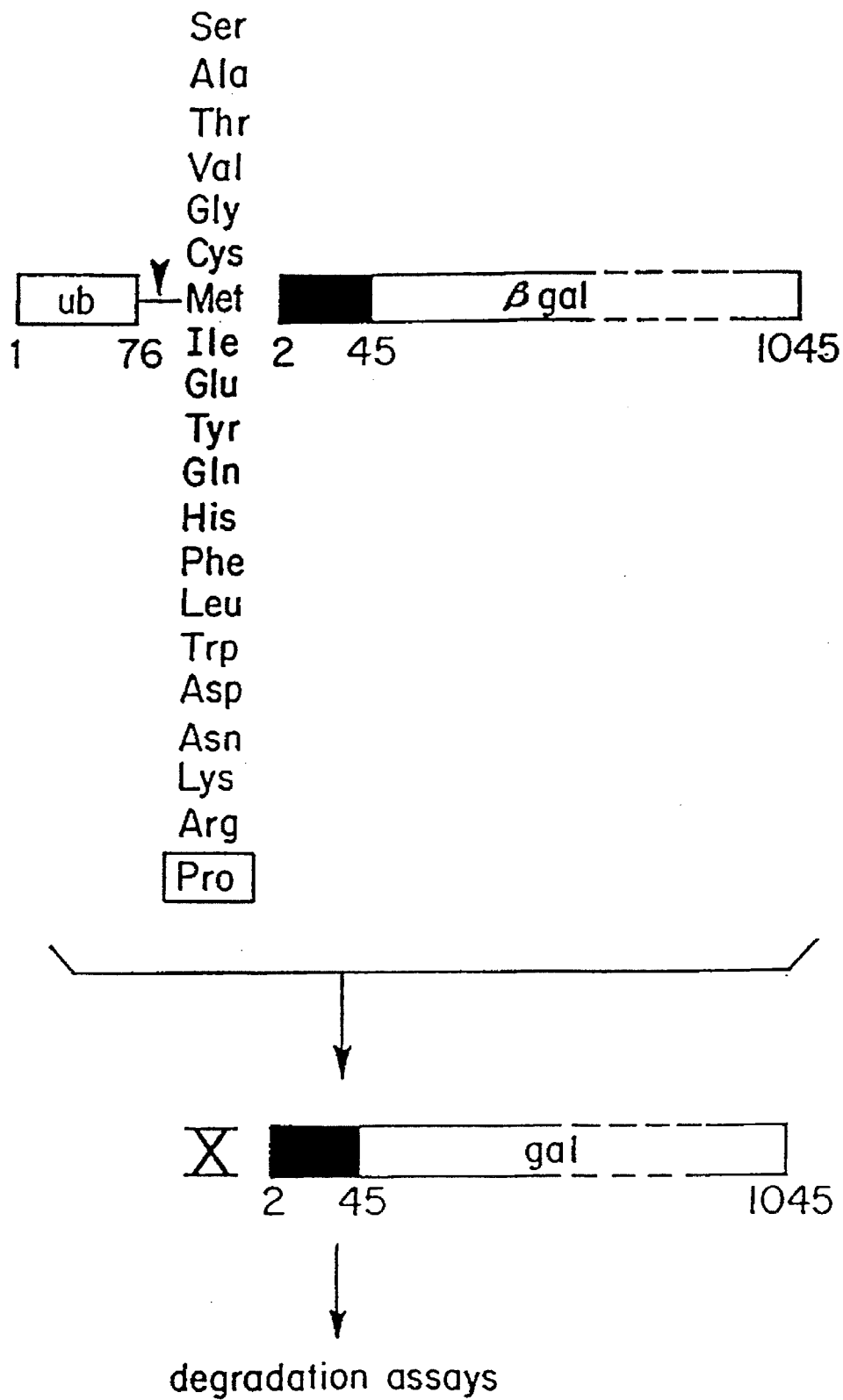
Figure 7B:
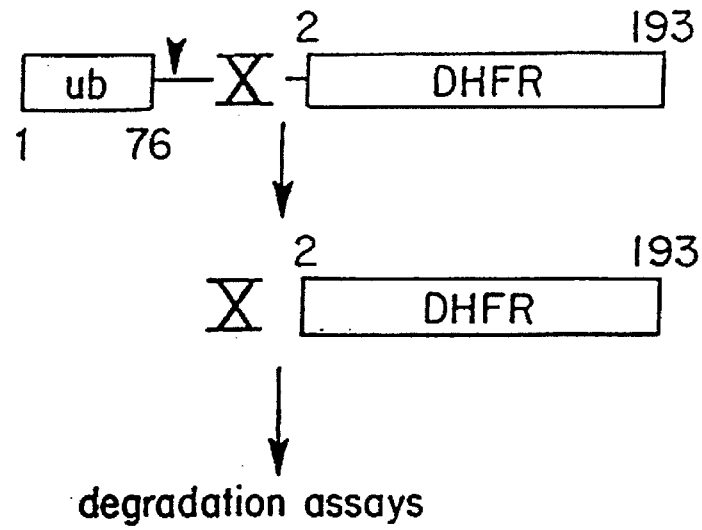

In a set of Ub fusions constructed with mouse dihydrofolate reductase (DHFR), a monomeric ~20-kd protein whose structure is known at atomic resolution, the mature amino-terminus of the "natural" DHFR is extended by 7 residues due to a construction route taken (FIG. 7). After cleavage of Ub from the nascent ubiquitin-DHFR fusion proteins in vivo, the deubiquitinated DHFR proteins differ exclusively at their amino-terminal residues. These constructions are analogous to the set of βgal test proteins (FIG. 3). As expected, the DHFR proteins bearing those amino-terminal residues that are stabilizing according to the N-end rule (Table 1) are long-lived in yeast (FIG. 7 and data not shown). Although the presence of a residue that is destabilizing according to the N-end rule at the amino-termini of an otherwise identical DHFR protein does destabilize it in vivo, the extent of destabilization is small (FIG. 7A) in comparison to the results with βgal of analogous design (Table 1). To address the mechanistic significance of these findings, a 40-residue amino-terminal region of βgal was positioned upstream of the original DHFR's amino-terminus (FIG. 7). The DHFR proteins bearing a destabilizing residue followed by the βgal-derived extension are approximately as short-lived in vivo as their unstable βgal counterparts, in striking contrast to the otherwise identical DHFR proteins that lack the βgal-specific amino-terminal extension (FIG. 7B and data not shown; cf. FIG. 7A). Furthermore, the extension-bearing DHFR proteins that have stabilizing residues at their amino-termini are long-lived in vivo (FIG. 7B). This latter result proves that the βgal-specific extension as such, in the absence of a destabilizing amino-terminal residue, does not confer a short half-life on DHFR. These findings also indicate that the reason for the striking difference between half-lives of the DHFR's that either lack or contain the βgal-specific extension (and bear identical, destabilizing amino-terminal residues) is due to differences in amino-terminal targeting elements in these proteins and not to differences between the overall structures of DHFR and βgal.

Figure 7C:
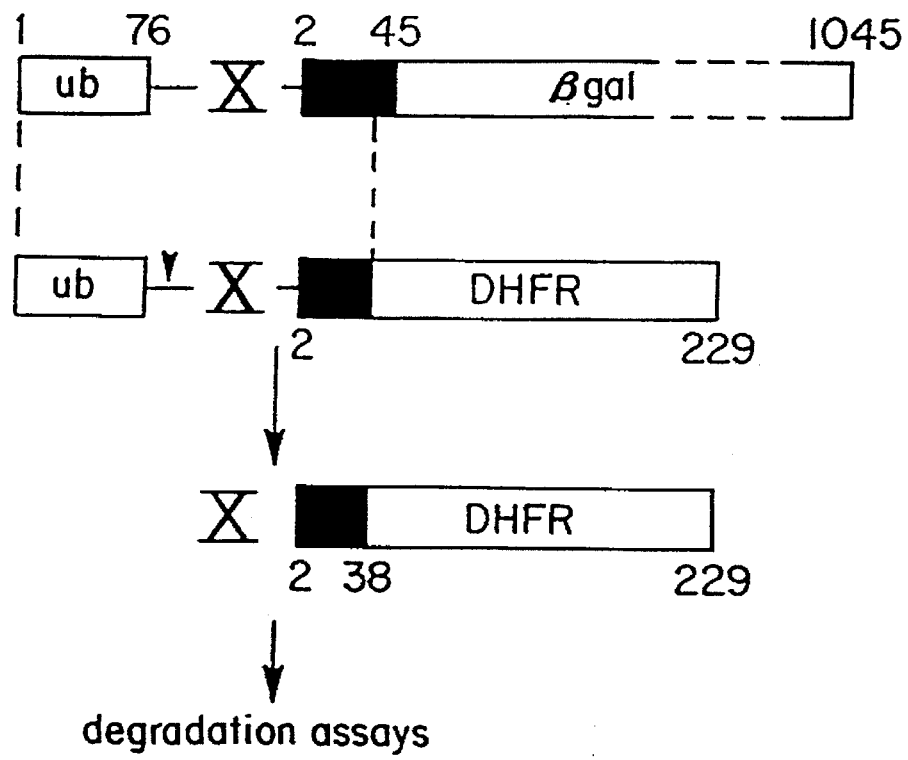

When DHFR is fitted with a 26-residue, βgal-derived amino-terminal extension instead of the original 40-residue extension, the dependence of the in vivo half-life of the resulting protein on the nature of its amino-terminal residue is intermediate between that of the original DHFR and that of the DHFR bearing a 36-residue βgal-derived extension (FIG. 7C; cf. FIG. 7B). Thus, the sequences required for the effect of the original βgal-specific extension are not confined to a short stretch within the extension but are distributed over the length of the extension. These insights indicate that the complete amino-terminal degradation signal contains a distinct determinant additional to the determinant represented by the amino-terminal amino acid residue. To address the nature of the second determinant in greater detail, a number of otherwise identical DHFR-based proteins bearing different variants of the βgal-derived extension and either a stabilizing or a destabilizing amino-terminal residue were expressed in the yeast *S. cerevisiae* and their half-lives determined (FIG. 8). The first conclusion from the data shown in FIG. 8 is that the two lysine (K) residues present in the βgal extension, although by themselves they do not render the protein metabolically unstable, are absolutely essential for conferring sensitivity to the N-end rule upon the test protein. Indeed, while the conversion of just one of the two lysine residues into a similarly charged arginine (R) residue still results in a protein whose half life is a strong function of its amino-terminal residue (structures II–IV in FIG. 8), the conversion of both lysine residues into arginine residues results in a long-lived test protein whose half-life is essentially insensisitive to the nature of its amino-terminal residue (Structure V in FIG. 8). At the same time, lysine residues are the only amino acid residues in proteins that can be posttranslationally joined to the carboxy-terminus of ubiquitin, with the formation of branched ubiquitin-protein conjugates. Strikingly, our direct determination of the positions of ubiquitin moieties in multiply ubiquitinated, short-lived proteins of the type shown in FIG. 8 has shown that all of the multiple ubiquitin moieties attached to a given molecule of the test protein reside in branched Ub—Ub structures attached to one of the two lysine residue that have been identified above by genetic methods as being essential components of the complete amino-terminal degradation signal. What then distinguishes the above lysine residues (Structures II–IV) from the numerous other lysine residues in the rest of the DHFR test protein? A clue to the unique role of the lysine residues as the second determinant of the amino-terminal degradation signal is provided by the fact that, due to the design of the original expression vector used in our work (see FIG. 1), our βgal test proteins bear a 45-residue amino-terminal extension derived from an internal sequence of the lac repressor encoded by the lacI gene.

Thus the "βgal-derived" amino-terminal extension discussed above (FIGS. 7 and 8) is derived not from the amino-terminal sequence of the wild-type βgal but from an unrelated sequence present at the amino-termini of our βgal test proteins. It is likely that the lac repressor-specific extension at the amino-termini of these βgals is more disordered (segmentally mobile) than the amino-terminal region of the wild-type βgal. If so, this extension, while not metabolically destabilizing βgal as such, could allow the observed extreme dependence of the βgal's half-life on the nature of its amino-terminal residue (Table 1), and thereby, in hindsight, could have greatly facilitated the discovery of the N-end rule. The disordered (segmentally mobile) state of the βgal extension provides an explanation for the unique nature of lysine residues within the extension versus the lysine residues in the spatially ordered DHFR portion of the test protein (FIG. 8). Thus, the simplest interpretation of this and related evidence is that the complete amino-terminal degradation signal comprises not one but two distinct determinants, each of which is necessary but by itself not sufficient to render the protein metabolically unstable. One determinant, described in the first part of this application, is the protein's amino-terminal residue. The second determinant, described immediately above, is a specific internal lysine residue. As indicated by the data of FIG. 8 and the considerations above, the ability of this critical lysine residue to serve as the second determinant is to a significant degree independent of the unique amino acid sequences surrounding the lysine residue. Instead, an essential feature of the critical lysine residue includes its spatial proximity to the protein's amino-terminus.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A non-naturally occuring fusion protein produced by recombinant DNA techniques, the fusion protein being encoded by a gene construct, the gene construct comprising a DNA sequence encoding ubiquitin joined to a DNA sequence encoding a protein or polypeptide of interest having a predetermined amino acid residue at its amino terminus, the ubiquitin being proteolytically cleavable by a ubiquitin-specific endoprotease at the junction with the amino-terminus of the protein or polypeptide of interest such that cleavage results in the exposure of the predetermined amino-terminal residue of the protein or polypeptide of interest, the amino-terminal residue being selected from the group consisting of valine, methionine, glycine and proline.

* * * * *

UNITED STATES PATENT AND TRADEMARK OFFICE
CERTIFICATE OF CORRECTION

PATENT NO. : 5,646,017
DATED : July 8, 1997
INVENTOR(S) : Bachmair et al.

It is certified that error appears in the above-indentified patent and that said Letters Patent is hereby corrected as shown below:

In column 1, between the Title and the Related Applications section, the following Government Support section should appear.

--- Government Support

This invention was made with government support under Contract Number NIH-2-R01-GM31530 awarded by the National Institutes of Health. The government has certain rights in the invention. ---

Signed and Sealed this

Eleventh Day of November, 1997

Attest:

BRUCE LEHMAN

Attesting Officer

Commissioner of Patents and Trademarks